(12) United States Patent
Han et al.

(10) Patent No.: US 8,945,723 B2
(45) Date of Patent: *Feb. 3, 2015

(54) ORGANOMETALLIC COMPLEXES AND ORGANIC ELECTROLUMINESCENCE DEVICE USING THE SAME

(75) Inventors: Eun-Sil Han, Daejeon-si (KR); Das Rupasree Ragini, Suwon-si (KR); Seok Chang, Daejeon-si (KR); Yi-Yeol Lyu, Daejeon-si (KR); Jong-Hyoup Lee, Seoul (KR); Hae-Jung Son, Seoul (KR); Lyong-Sun Pu, Suwon-si (KR); Tae-Yong Noh, Gunpo-si (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 1659 days.

This patent is subject to a terminal disclaimer.

(21) Appl. No.: 12/081,214

(22) Filed: Apr. 11, 2008

(65) Prior Publication Data

US 2008/0265758 A1  Oct. 30, 2008

Related U.S. Application Data

(62) Division of application No. 10/979,110, filed on Nov. 2, 2004, now Pat. No. 7,378,161.

(30) Foreign Application Priority Data

Nov. 6, 2003 (KR) .................................. 2003-78329

(51) Int. Cl.
| | |
|---|---|
| H01L 51/54 | (2006.01) |
| C09K 11/06 | (2006.01) |
| C07F 15/00 | (2006.01) |
| H01L 51/00 | (2006.01) |
| H05B 33/14 | (2006.01) |
| H01L 51/50 | (2006.01) |

(52) U.S. Cl.
CPC ............ *C09K 11/06* (2013.01); *C07F 15/0033* (2013.01); *H01L 51/0085* (2013.01); *H05B 33/14* (2013.01); *C09K 2211/1029* (2013.01); *C09K 2211/1044* (2013.01); *C09K 2211/185* (2013.01); *H01L 51/5016* (2013.01); *H01L 51/5036* (2013.01); *Y10S 428/917* (2013.01)
USPC .... 428/690; 428/917; 313/504; 257/E51.044; 548/101; 548/402; 546/4

(58) Field of Classification Search
None
See application file for complete search history.

(56) References Cited

U.S. PATENT DOCUMENTS

| | | | |
|---|---|---|---|
| 6,383,666 B1 | 5/2002 | Kim et al. | |
| 7,378,161 B2 * | 5/2008 | Han et al. | 428/690 |
| 7,396,599 B2 * | 7/2008 | Lyu et al. | 428/690 |
| 2002/0048689 A1 | 4/2002 | Igarashi et al. | |
| 2002/0064681 A1 | 5/2002 | Takiguchi et al. | |
| 2002/0068190 A1 | 6/2002 | Tsuboyama et al. | |
| 2002/0182441 A1 | 12/2002 | Lamansky et al. | |
| 2003/0040627 A1 | 2/2003 | Fujii | |
| 2003/0143428 A1 | 7/2003 | Kim et al. | |
| 2004/0102632 A1 | 5/2004 | Thompson et al. | |
| 2005/0176624 A1 | 8/2005 | Thompson et al. | |

FOREIGN PATENT DOCUMENTS

| | | |
|---|---|---|
| CN | 1302302 A | 7/2001 |
| CN | 1397559 A | 2/2003 |
| CN | 1427654 A | 7/2003 |
| CN | 1454448 | 11/2003 |
| WO | WO 02/15645 | 2/2002 |

OTHER PUBLICATIONS

Baldo, et al., "Highly efficient phosphorescent emission from organic electroluminescent devices", Nature, vol. 395, pp. 151-154; Sep. 10, 1998.
Adachi, et al., "High-efficiency organic electrophosphorescent devices with tris(2-phenylpyridine)iridium doped into electron-tansporting materials", Applied Physics Letters, vol. 77, No. 6, pp. 904-906; Aug. 7, 2000.
Baldo, et al., "Very high-efficiency green organic light-emitting devices based on electrophosphorescence", Applied Physics Letters, vol. 75, No. 1, pp. 4-6; Jul. 5, 1999.
Adachi, et al., "High-efficiency red electrophosphorescence devices", Applied Physics Letters, vol. 78, No. 11, pp. 1622-1624; Mar. 12, 2001.
Chinese Office action corresponding to Chinese Patent Application No. 200410089709X, issued on Dec. 15, 2006.
U.S. Appl. No. 60/493,144 to Thompson et al., entitled Heavy Metal Complexes as Singlet Oxygen Sensitizers, filed Aug. 7, 2003.
Jian Li et al., "Synthesis and characterization of cyclometalated Ir(III) complexes with pyrazolyl ancillary ligands", Polyhedron 23 (2004) 419-428.
F. O. Garces et al., "Synthesis, Structure, Electrochemistry, and Photophysics of Methyl-Substituted Phenylpyridine Ortho-Metalated Iridium(III) Complexes", Inorg. Chem. 1988, 27, 3464-3471.
S. Sprouse et al., "Photophysical Effects of Metal-Carbon α Bonds in Ortho-Metalated Complexes of Ir(III) and Rh(III)", J. Am. Chem. Soc. 1984, 106, 6647-6653.
Chinese Registration Determination Certificate issued by the Chinese Intellectual Property Office on Dec. 9, 2009 in the corresponding Chinese Patent No. ZL200410089709.X.

* cited by examiner

*Primary Examiner* — Marie R. Yamnitzky
(74) *Attorney, Agent, or Firm* — Robert E. Bushnell, Esq.

(57) ABSTRACT

An organometallic complex that increases an energy band gap between HOMO and triplet MLCT states, and enables highly efficient phospholuminescence and can be used for an organic electroluminescent device. The organometallic complex, which is suitably used for forming an organic layer of the organic electroluminescent device, provides a luminescence maximum emission in the wavelength range of 400-650 nm, and induces white electroluminescence when combined with green or red luminescent materials.

15 Claims, 3 Drawing Sheets

ORGANOMETALLIC COMPLEXES AND ORGANIC ELECTROLUMINESCENCE DEVICE USING THE SAME

CLAIM OF PRIORITY AND CROSS-REFERENCE TO RELATED APPLICATION

This application claims all benefits accruing under 35 U.S.C. §119 from the Korean Patent Application No. 2003-78329, filed Nov. 6, 2003, in the Korean Intellectual Property Office, the disclosure of which is incorporated herein in its entirety by reference. Furthermore, this application is a divisional of Applicants' Ser. No. 10/979,110 filed in the U.S. Patent & Trademark Office on 2 Nov. 2004, now U.S. Pat. No. 7,378,161, and assigned to the assignee of the present invention.

BACKGROUND OF THE INVENTION

1. Field of the Invention

The present invention relates to organometallic complexes and an organic electroluminescence device using the same, and more particularly, to organometallic complexes capable of emitting light over a wide range from a blue region to a red region through triplet metal-to-ligand charge transfer (MLCT) and an organic electroluminescence device using the same as an organic layer forming material 2. Description of the Related Art Generally, an organic electroluminescent (hereinafter referred to as EL, hereinafter) device is a spontaneous light-emitting display device which emit light by energy generated through recombination of electrons and holes when an electric field is applied to thin films made of fluorescent or phosphorescent organic compounds (to be referred to as organic layers, hereinafter). The organic EL device has good lightness, constructional simplicity, high color purity, perfect implementation of motion pictures, low power consumption, a low driving voltage, and so on, and the organic EL device is suitable to be used for portable electronic devices.

A general organic EL device includes an anode, a hole injection layer, a hole transport layer, a light-emitting layer, an electron transport layer an electron injection layer, and a cathode, which are sequentially formed on a substrate. The hole transport layer, the light-emitting layer, and the electron transport layer are organic layers made of organic compounds. The organic EL device having the above-described configuration is driven as follows. When a voltage is applied between the anode and the cathode, holes injected from the anode migrate to the light-emitting layer via the hole transport layer. Electrons emitted from the cathode are injected into the light-emitting layer via the electron transport layer. The electrons and the holes recombine in the light-emitting layer to generate excitons. While the excitons are radioactively decaying, light with a wavelength corresponding to a band gap of the molecules is emitted.

Materials for forming the light-emitting layer of the organic EL device are classified into a fluorescent material which uses a singlet exciton and a phosphorescent material which uses a triplet exciton, according to a light-emitting mechanism. The fluorescent material or the phosphorescent material forms a light-emitting layer by itself or by being doped to an appropriate host material. As a result of electron excitation, singlet excitons and triplet excitons are produced in the host. Statistically, the singlet excitons and the triplet excitons in an OLED are created in a ratio of about 1:3. Conventional organic EL devices using a fluorescent material as a material for forming a light-emitting layer are disadvantageous in that triplet excitons are consumed from the host. However, conventional organic EL devices using a phosphorescent material as a material for forming a light-emitting layer are advantageous in that singlet excitons and triplet excitons are both utilized to achieve the internal quantum efficiency of 100%. Thus, an organic EL device using a phosphorescent material as a material for forming a light-emitting layer has a high emission efficiency compared with an organic EL device using a fluorescent material.

Introduction of a heavy metal such as Ir, Pt, Rh, or Pd to organic molecules has led to spin-orbital coupling due to a heavy atom effect so that a triplet state and a singlet state coexist, enabling a forbidden transition and phospholuminescence to occur even at room temperature.

More recently, developments have led to the discovery of high-efficiency green and red phosphorescence materials with the improved internal quantum efficiency as discussed by the following articles; Baldo, et al., Nature, vol. 395, 151-154, 1998; Baldo, et al., Appl. Phys. Lett., 75, 4-6, 1999; Adachi, et al., Appl. Phys. Lett., 77, 904-906, 2000; Adachi, et al., Appl. Phys. Lett., 78, 1622-1624, 2001. In particular, a green phospholuminescent (PL) material using fac tris(2-phenylpyridine)iridium ($Ir(ppy)_3$) has an external quantum efficiency of 17.6±0.5%. Bis(2-(2'-benzo[4,5-α]thienyl)pyridinato-N,C) iridium (acetylacetonate) ($Btp_2Ir(acac)$) has been reported as a red EL material having a maximum external quantum efficiency of 7.0±0.5%.

As described above, as highly efficient luminescent materials using phospholuminescence, various materials employing various transition metal complexes containing a transition metal such as iridium or platinum, have been being reported. However, materials satisfying requirements for realizing a full-color display of high emission efficiency or white electroluminescence with low power consumption are only restricted to ones emitting in the green and red ranges, and blue phosphorescent materials have not been reported, making it difficult to achieve a full-color display, which is, in turn, becoming a barrier to development of phospholuminescent full-color display devices.

To address the above-described problems, intensive development of blue luminescent materials is under way (WO 02/15645 A1 entitled Organometallic Compounds and Emission-Shifting Organic Electrophosphorescence and published Feb. 21, 2002, U.S. Patent Publication. No. 2002/0064681 A1 entitled Luminescence Device, Display Apparatus and Metal Coordination Compound and published on May 30, 2002). Also, there have been proposed organometallic complexes having a bulky functional group or a functional group having a high intensity ligand field, e.g., a cyano group, introduced thereto to increase a difference between the energy levels of the highest energy occupied molecular orbital and the lowest energy occupied molecular orbital (HOMO-LUMO energy levels) by transforming the molecular geometry. Another materials that have recently been developed include iridium complexes having the general formula of $Ir(ppy)_2P(ph)_3Y$, where Y=Cl or CN, as described in US2002/0182441 A1 entitled Organometallic Compounds and Emission-Shifting Organic Electrophosphorescence and published on Dec. 5, 2002, and iridium (III) complexes having a cyclometalating ligand and chelating diphosphine, chlorine and cyano group, as described in U.S. Patent Publication No. 2002/0048689 A1 entitled Light-Emitting Device and Iridium Complex and published on Apr. 25, 2002.

SUMMARY OF THE INVENTION

It is therefore an object of the present invention to provide organometallic complexes capable of emitting light over a wide wavelength range from a blue region to a red region through triplet metal-to-ligand charge transfer (MLCT) and an organic electroluminescence device using the same as an organic layer forming material.

It is also an object of the present invention to provide an improved organic EL device using the organometallic complex.

In an aspect of the present invention, there is provided an organometallic complex represented by Formula 1:

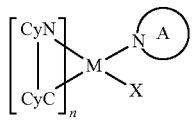

[Formula 1]

wherein M is a metal selected from the group consisting of Ir, Os, Pt, Pb, Re, Ru, and Pd;

CyN is a substituted or unsubstituted $C_3$-$C_{60}$ heterocyclic group containing nitrogen bonded to M, or a substituted or unsubstituted $C_3$-$C_{60}$ heteroaryl group containing nitrogen bonded to M;

CyC is a substituted or unsubstituted $C_4$-$C_{60}$ carbocyclic group containing carbon bonded to M, substituted or unsubstituted $C_3$-$C_{60}$ heterocyclic group containing carbon bonded to M, substituted or unsubstituted $C_3$-$C_{60}$ aryl containing carbon bonded to M, or substituted or unsubstituted $C_3$-$C_{60}$ heteroaryl containing carbon bonded to M;

each substituent of the CyN-CyC is independently a halogen atom, —OR, —N(R)(R'), —P(R)(R'), —POR, —PO$_2$R, —PO$_3$R, —SR, —Si(R)(R')(R''), —B(R)(R'), —B(OR)(OR'), —C(O)R, —C(O)OR, —C(O)N(R), —CN, —NO$_2$, —SO$_2$, —SOR, —SO$_2$R, —SO$_3$R, substituted or unsubstituted $C_1$-$C_{20}$ alkyl, or substituted or unsubstituted $C_6$-$C_{20}$ aryl, the substituents are alternatively joined to form a substituted or unsubstituted 4- to 7-membered carbocyclic group or a substituted or unsubstituted 4- to 7-membered heterocyclic group, the R, R' and R'' are independently selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

alternatively, the CyN-CyC is represented by the following Formula:

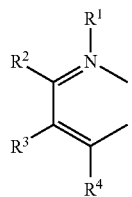

[Formula 1a]

wherein $R^1$, $R^2$, $R^3$, and $R^4$ are independently a mono-substituted or multi-substituted group, and $R^1$, $R^2$, $R^3$, and $R^4$ are independently selected from the group consisting of hydrogen, halogen atom, —OR$^a$, —N(R$^a$)$_2$, —P(R$^a$)$_2$, —POR$^a$, —PO$_2$R$^a$, —PO$_3$R$^a$, —SR$^a$, —Si(R$^a$)$_3$, —B(R$^a$)$_2$, —B(OR$^a$)$_2$, —C(O)R$^a$, —C(O)OR$^a$, —C(O)N(R$^a$), —CN, —NO$_2$, —SO$_2$, —SOR$^a$, —SO$_2$R$^a$, —SO$_3$R$^a$, $C_1$-$C_{20}$ alkyl, or $C_6$-$C_{20}$ aryl, R$^a$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

A is a ligand containing nitrogen bonded to M;

X is a monoanionic monodentate ligand; and n is 1 or 2.

In another feature of an embodiment of the present invention, there is provided an organic electroluminescent device comprising an organic layer between a pair of electrodes, wherein the organic layer comprises the above organometallic complex.

DETAILED DESCRIPTION OF THE INVENTION

Figure 1:
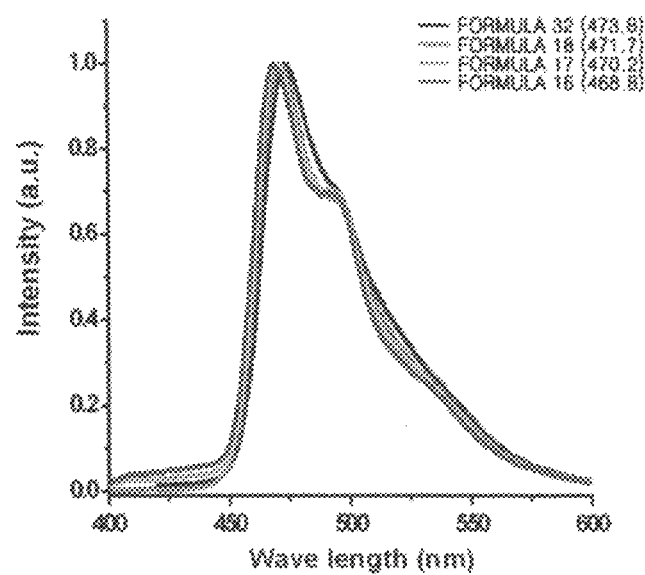
FIG. 1 shows photoluminescence (PL) spectra of compounds represented by Formulas 32 and 16 through 18.

Reference will now be made in detail to the present preferred embodiments of the present invention.

An organometallic complex according to the present invention is represented by Formula 1:

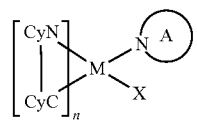

[Formula 1]

wherein

M is a metal selected from the group consisting of Ir, Os, Pt, Pb, Re, Ru, and Pd;

CyN is a substituted or unsubstituted $C_3$-$C_{60}$ heterocyclic group containing nitrogen bonded to M, or a substituted or unsubstituted $C_3$-$C_{60}$ heteroaryl group containing nitrogen bonded to M;

CyC is a substituted or unsubstituted $C_4$-$C_{60}$ carbocyclic group containing carbon bonded to M, substituted or unsubstituted $C_3$-$C_{60}$ heterocyclic group containing carbon bonded to M, substituted or unsubstituted $C_3$-$C_{60}$ aryl containing carbon bonded to M, or substituted or unsubstituted $C_3$-$C_{60}$ heteroaryl containing carbon bonded to M;

each substituent of the CyN-CyC is independently a halogen atom, —OR, —N(R)(R'), —P(R)(R'), —POR, —PO$_2$R, —PO$_3$R, —SR, —Si(R)(R')(R''), —B(R)(R'), —B(OR)(OR'), —C(O)R, —C(O)OR, —C(O)N(R), —CN, —NO$_2$, —SO$_2$, —SOR, —SO$_2$R, —SO$_3$R, substituted or unsubstituted C$_1$-C$_{20}$ alkyl, or substituted or unsubstituted C$_6$-C$_{20}$ aryl, the substituents are alternatively joined to form a substituted or unsubstituted 4- to 7-membered carbocyclic group or a substituted or unsubstituted 4- to 7-membered heterocyclic group, the R, R' and R'' are independently selected from the group consisting of hydrogen, a substituted or unsubstituted C$_1$-C$_{20}$ alkyl, substituted or unsubstituted C$_1$-C$_{20}$ alkoxy, substituted or unsubstituted C$_2$-C$_{20}$ alkenyl, substituted or unsubstituted alkynyl, substituted or unsubstituted C$_1$-C$_{20}$ heteroalkyl, substituted or unsubstituted C$_6$-C$_{40}$ aryl, substituted or unsubstituted C$_7$-C$_{40}$ arylalkyl, substituted or unsubstituted C$_7$-C$_{40}$ alkylaryl, substituted or unsubstituted C$_2$-C$_{40}$ heteroaryl, and substituted or unsubstituted C$_3$-C$_{40}$ heteroarylalkyl;

alternatively, the CyN-CyC is represented by the following Formula:

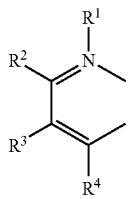

[Formula 1a]

wherein

R$^1$, R$^2$, R$^3$, and R$^4$ are independently a mono-substituted or multi-substituted group, and R$^1$, R$^2$, R$^3$, and R$^4$ are independently selected from the group consisting of hydrogen, halogen atom, —OR$^a$, —N(R$^a$)$_2$, —P(R$^a$)$_2$, —POR$^a$, —PO$_2$R$^a$, PO$_3$R$^a$, —SR$^a$, —Si(R$^a$)$_3$, —B(R$^a$)$_2$, —B(OR$^a$)$_2$, —C(O)R$^a$, —C(O)OR$^a$, —C(O)N(R$^a$), —CN, —NO$_2$, —SO$_2$, —SOR$^a$, —SO$_2$R$^a$, —SO$_3$R$^a$, C$_1$-C$_{20}$ alkyl, or C$_6$-C$_{20}$ aryl, R$^a$ is selected from the group consisting of hydrogen, a substituted or unsubstituted C$_1$-C$_{20}$ alkyl, substituted or unsubstituted C$_1$-C$_{20}$ alkoxy, substituted or unsubstituted C$_2$-C$_{20}$ alkenyl, substituted or unsubstituted C$_2$-C$_{20}$ allynyl, substituted or unsubstituted C$_1$-C$_{20}$ heteroalkyl, substituted or unsubstituted C$_6$-C$_{40}$ aryl, substituted or unsubstituted C$_7$-C$_{40}$ arylalkyl, substituted or unsubstituted C$_7$-C$_{40}$ alkylaryl, substituted or unsubstituted C$_2$-C$_{40}$ heteroaryl, and substituted or unsubstituted C$_3$-C$_{40}$ heteroarylalkyl;

A is a ligand containing nitrogen bonded to M;

X is a monoanionic monodentate ligand; and n is 1 or 2.

An organometallic complex represented by Formula 1 according to the present invention increases an energy band gap between HOMO and triplet MLCT states, enabling blue electroluminescence. The increased energy band gap between HOMO level and triplet MLCT level allows coordination to a bulky ligand, leading to a twisted geometry. An increase in the energy band gap is allowed by introduction of a ligand capable of providing a strong ligand field exhibiting excellent an σ-donor or π-donor capability. In Formula 1, when X is a cyanide ion (CN—), the cyanide ion is capable of providing a strong ligand field, and reduces the HOMO energy level, leading to a shift of the emission wavelength range toward the blue range.

In Formula 1, the heterocyclic group represents a cyclic group containing a hetero atom such as N, O, or S, and the heteroaryl group represents an aryl group containing a hetero atom such as N, O, or S.

In CyN of Formula 1, specific examples of the C$_3$-C$_{60}$ heterocyclic group containing nitrogen bonded to M include pyrrolidine, morpholine, thiomorpholine, thiazolidine and the like, and specific examples of the substituted or unsubstituted C$_3$-C$_{60}$ heteroaryl group containing nitrogen bonded to M include pyridine, 4-methoxy pyridine, quinoline, pyrrole, indole, pyrazine, pyrazole, imidazole, pyrimidine, quinazoline, thiazole, oxazole, triazine, 1,2,4-triazole and the like.

In CyC of Formula 1, specific examples of the substituted or unsubstituted C$_4$-C$_{60}$ carbon ring group containing carbon bonded to M include cyclohexane, cyclopentane and the like. Specific examples of the substituted or unsubstituted C$_3$-C$_{60}$ heterocyclic group containing carbon bonded to M include tetrahydrofuran, 1,3-dioxane, 1,3-dithiane, 1,3-dithiolane, 1,4-dioxa-8-azaspiro[4,5]decane, 1,4-dioxaspiro[4,5]decan-2-one and the like. Specific examples of the substituted or unsubstituted C$_3$-C$_{60}$ aryl containing carbon bonded to M include phenyl, 1,3-(benzodioxole), biphenyl, naphthalene, anthracene, azulene and the like. Specific examples of the substituted or unsubstituted C$_3$-C$_{60}$ heteroaryl containing carbon bonded to M include thiophene, furan2(5H)-furanone, pyridine, coumarin, imidazole, 2-phenylpyridine, 2-benzothiazole, 2-benzooxazole, 1-phenylpyrazole, 1-naphthylpyrazole 1-naphthylpyrazole,5-(4-methoxyphenyl)pyrazole, 2,5-bisphenyl-1,3,4-oxadiazole, 2,3-benzofuran2-(4-biphenyl)-6-phenyl benzooxazole, and the like.

In Formula 1, the respective substituents of CyN—CyC are interconnected to form a substituted or unsubstituted 4- to 7-membered carbocyclic group or substituted or unsubstituted 4- to 7-membered heterocyclic group, in particular, a fused 4- to 7-membered carbocyclic or heterocyclic group. Here, the carbocyclic group or hetero cyclic group represents a C$_1$-C$_{30}$ cycloalkyl, C$_1$-C$_{30}$ heterocycloalkyl, C$_6$-C$_{30}$ aryl or C$_4$-C$_{30}$ heteroallyl, each cyclic group or heterocyclic group can be substituted by one or more substituents Y. The term "hetero" used herein is intended to encompass a hetero atom such as N, O, P, or S.

Y represents a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, or —SO$_3$R, and R is defined as above.

A represents a monocathionic, monodentate ligand containing nitrogen bonded to M, and X represents a monoanionic ligand such as F, Cl, Br, I, CN, CN(R), SCN, or OCN.

Examples of the nitrogen-containing A bonded to M include, but are not limited to, a compound derived from at least one selected from the group consisting of substituted or unsubstituted triethylamine, propylamine, cyclohexylamine, pyrrolidine, pyrroline, piperidine, pyrimidine, indole, azaindole, carbazole, indazole, norharman, harman, aniline, imidazole, oxazole, thiazole, pyrazole, pyrrole, benzimidazole, benzotriazole, benzoxazole, benzothiazole, benzoselenazole, benzothiadioxole, isoxazole, isothiazole, oxadiazole, thiadiazole, anthranyl, triazine, benzisoxazole, pyrazine, quinoline, benzoquinoline, acridine, thiazoline, quinuclidine, imidazoline, oxazoline, thiazoline, and isoquinoline.

The CyN-CyC can be represented by the following Formulas, but is not limited thereto.

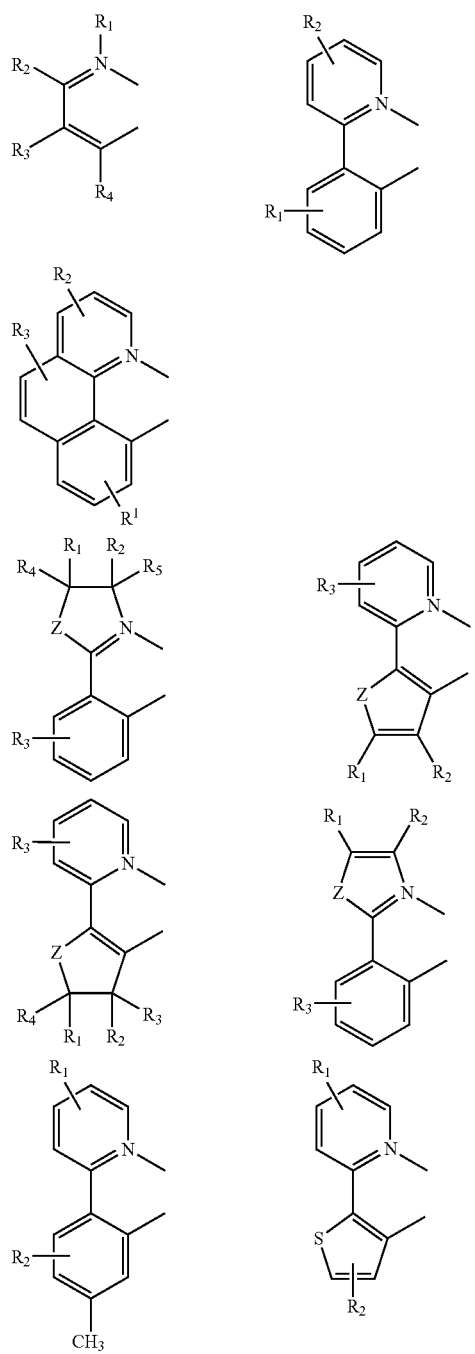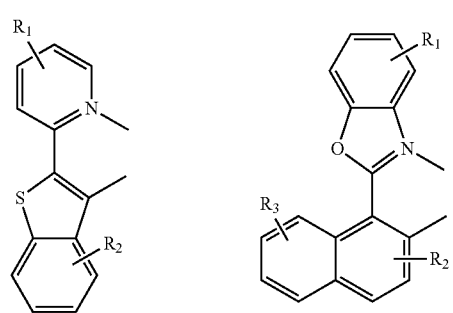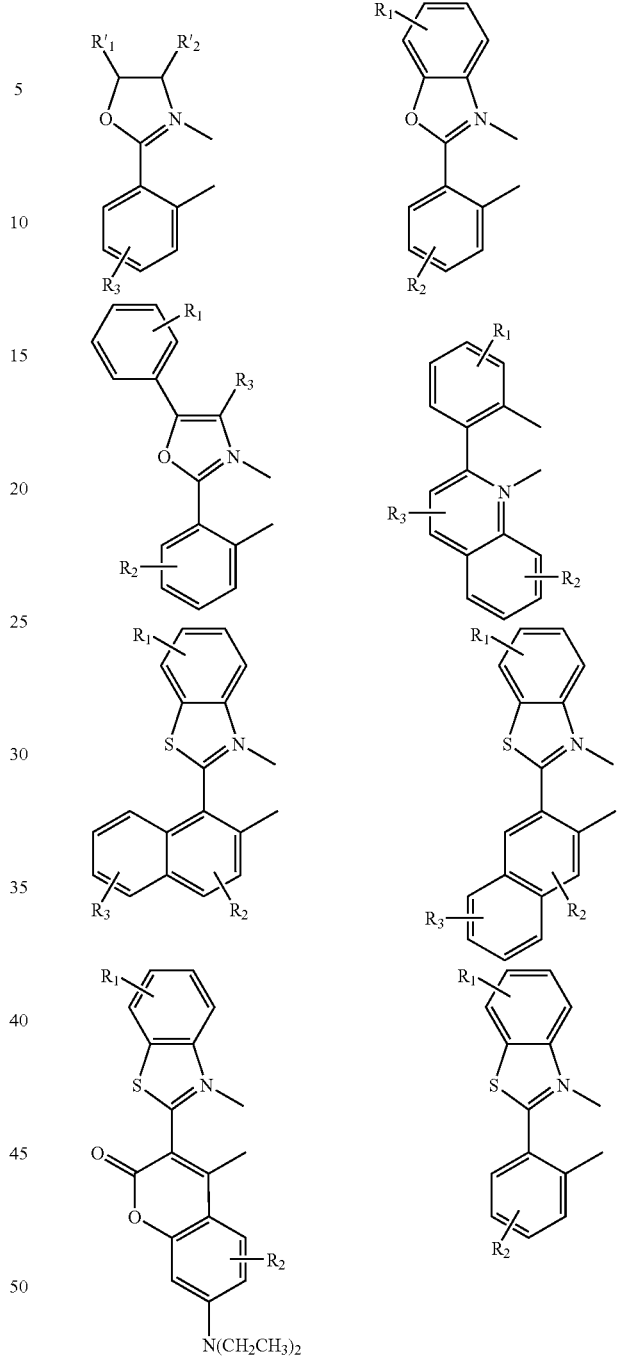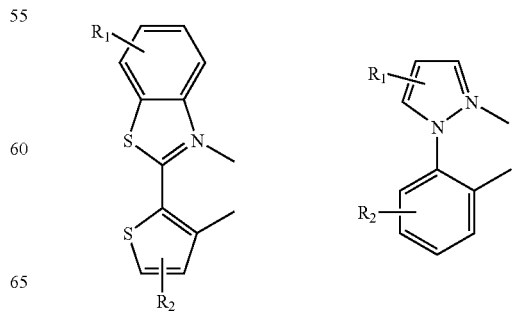

-continued

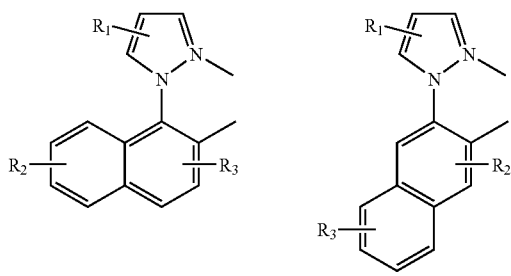

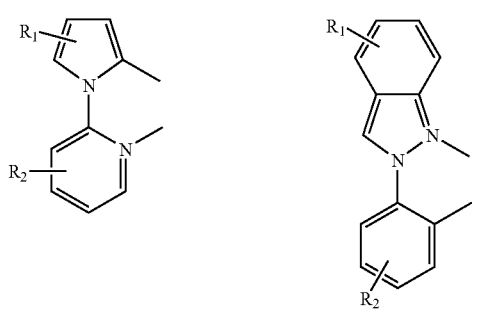

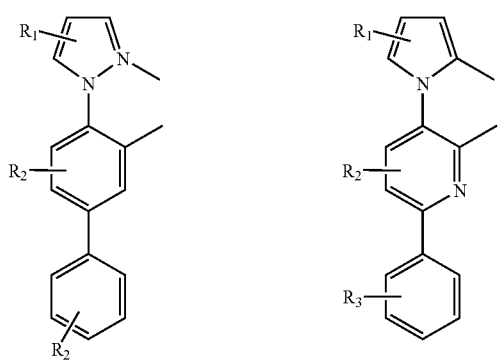

wherein $R_1$, $R_2$, $R_3$, $R_4$, and $R_5$ of the above formula representing CyN—CyC are independently a mono-substituted or multi-substituted group, and $R_1$, $R_2$, $R_3$, 4 and $R_5$ are independently selected from the group consisting of hydrogen, halogen atom, —$OR^b$, —$N(R)_2$, —$P(R^b)_2$, —$POR^b$, —$PO_2R^b$, —$PO_3R^b$, —$SR^b$, —$Si(R^b)_3$, —$B(OR^b)$, —$C(O)R^b$, —$C(O)OR^b$, —$C(O)N(R)$, —$CN$, —$NO_2$, —$SO_2$, —$SOR^b$, —$SO_2R^b$, —$SO_3R^b$, a $C_1$-$C_{20}$ alkyl group, or a $C_6$-$C_{20}$ aryl group;

$R^b$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl; and Z is S, O, or $NR_0$ where $R_0$ is hydrogen or a $C_1$-$C_{20}$ alkyl group.

Specific examples of the organometallic complex of Formula 1 include, but is not limited to, compounds represented by Formulas 2 through 14:

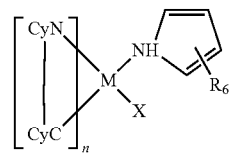
[Formula 2]

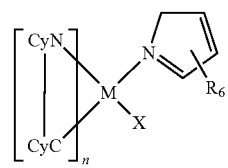
[Formula 3]

[Formula 4]

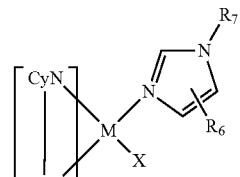
[Formula 5]

[Formula 6]

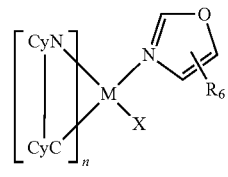

[Formula 7]

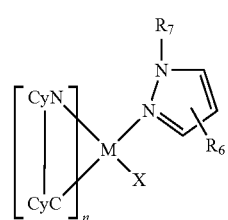

[Formula 8]

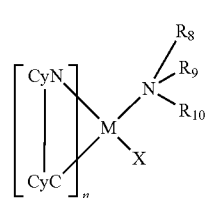

[Formula 9]

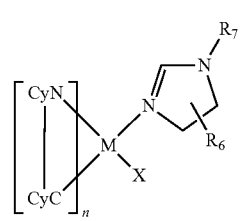

-continued

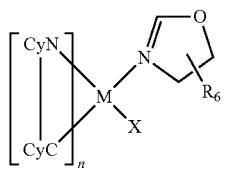
[Formula 10]

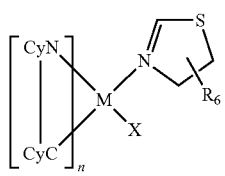
[Formula 11]

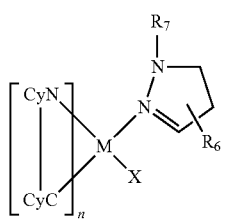
[Formula 12]

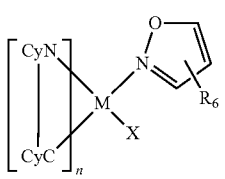
[Formula 13]

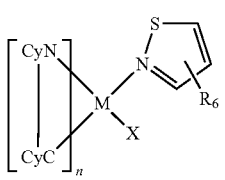
[Formula 14]

wherein

M and CyN—CyC are as defined as above;

$R_6$ and $R_7$ are independently a mono-substituted or multi-substituted group, and $R_6$ and $R_7$ are independently selected from the group consisting of hydrogen, halogen atom, —$OR^c$, —$N(R^c)_2$, —$P(R^c)_2$, —$POR^c$, —$PO_2R^c$, —$PO_3R^c$, —$SR^c$, —$Si(R^c)_3$, —$B(R^c)_2$, —$B(OR^c)_2$, —$C(O)R^c$, —$C(O)OR^c$, —$C(O)N(R^c)$, —CN, —$NO_2$, —$SO_2$, —$SOR^c$, —$SO_2R^c$, —$SO_3R^c$, substituted or unsubstituted $C_1$-$C_{20}$ alkyl, substituted or unsubstituted $C_6$-$C_{20}$ aryl or substituted or unsubstituted $C_2$-$C_{20}$ heteroaryl, and $R^c$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

substituents of $R_6$ and $R_7$, which are substituted at different positions, are interconnected to form a substituted or unsubstituted fused 4-7 atom ring;

$R_8$, $R_9$, and $R_{10}$ are independently a substituted or unsubstituted $C_1$-$C_{20}$ alkyl group, a substituted or unsubstituted $C_6$-$C_{20}$ aryl group or a substituted or unsubstituted $C_2$-$C_{20}$ heteroaryl group;

X is F, Cl, Br, I, CN, $CN(R_{11})$, SCN or OCN, $R_1$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl; and n is 1 or 2.

In Formula 1, M is preferably Ir or Pt.

Preferably, the organometallic complex of Formula 1 is one selected from the group consisting of compounds represented by Formula 15 through 35:

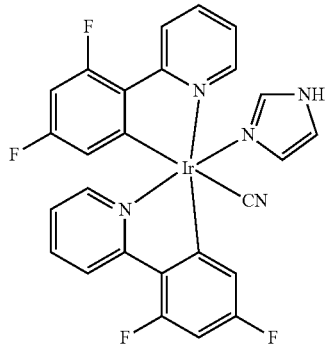
[Formula 15]

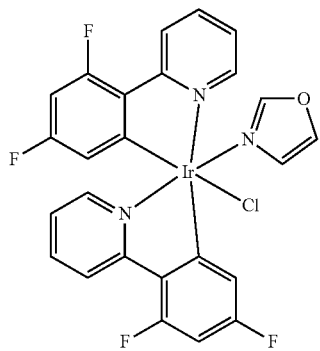
[Formula 16]

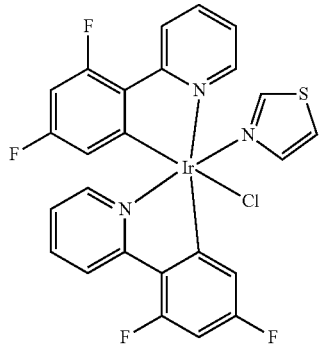
[Formula 17]

[Formula 18]
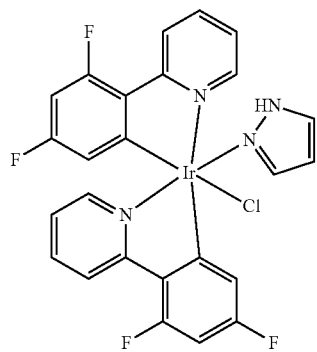
[Formula 19]
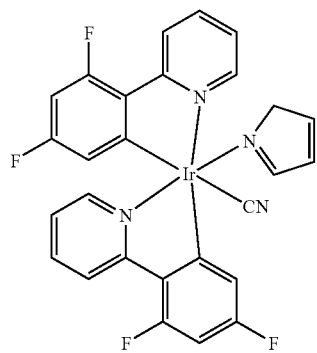
[Formula 20]
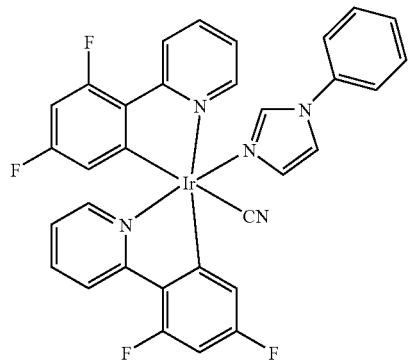
[Formula 21]
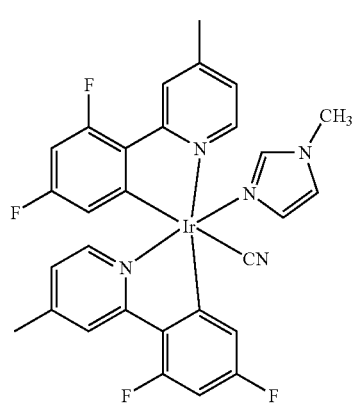
[Formula 22]
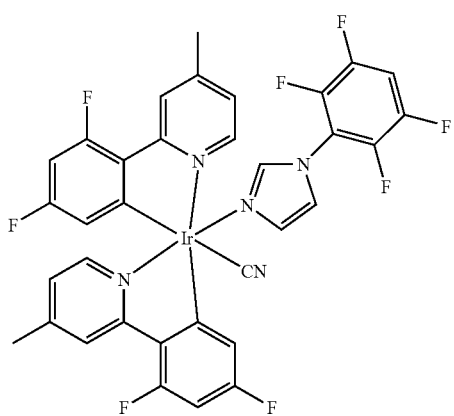
[Formula 23]
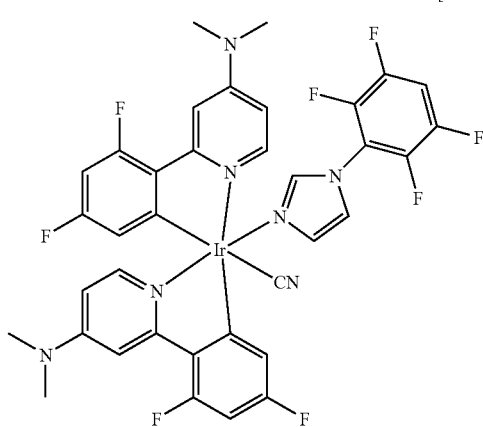
[Formula 24]
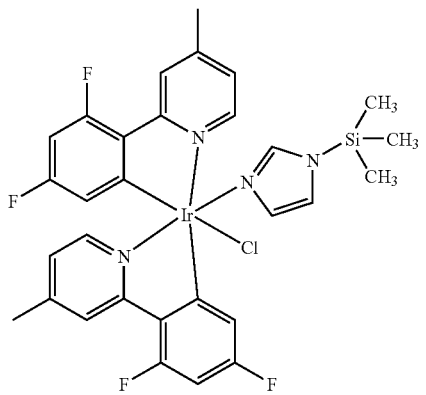
[Formula 25]
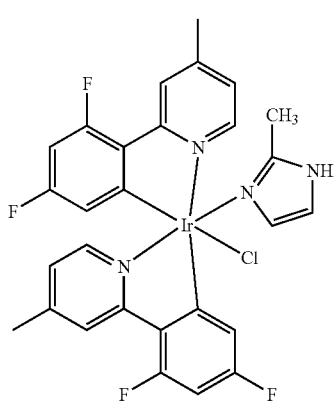

[Formula 26]
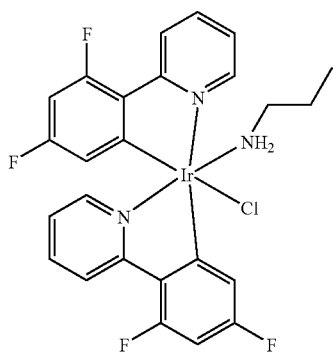
[Formula 27]
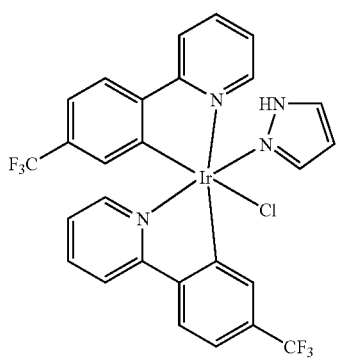
[Formula 28]
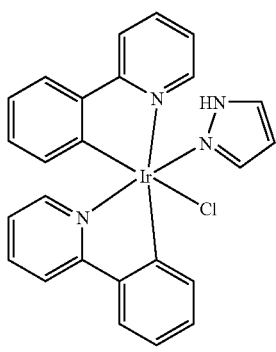
[Formula 29]
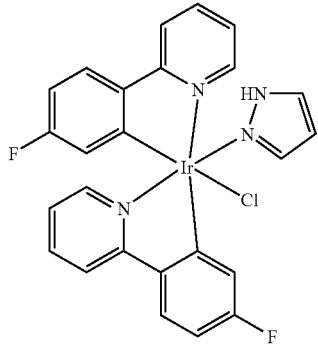
[Formula 30]
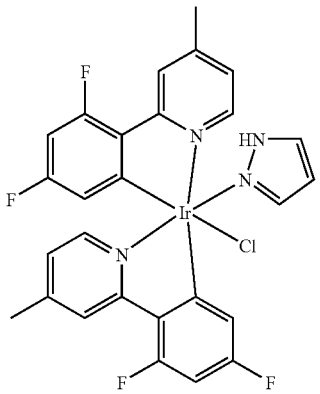
[Formula 31]
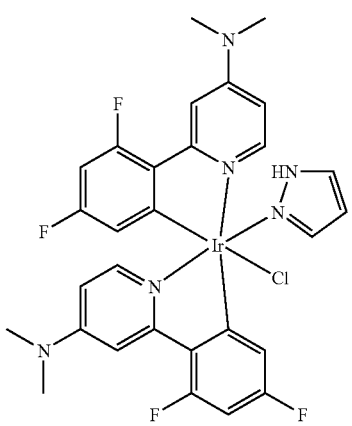
[Formula 32]
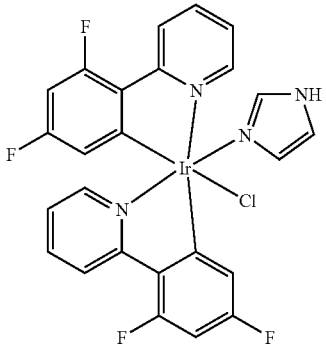
[Formula 33]
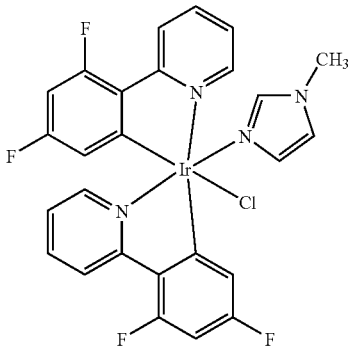

[Formula 34]

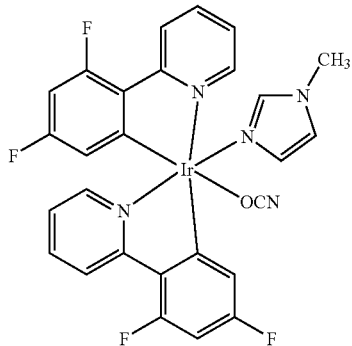

[Formula 35]

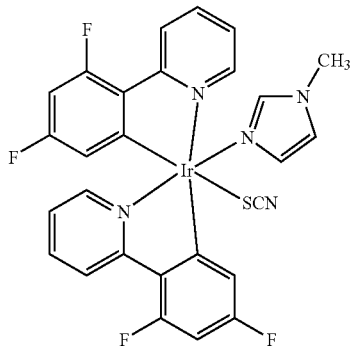

The compounds represented by Formula 1 according to the present invention provide a luminescence maximum emission in the wavelength range of 400-650 nm.

The organometallic complexes represented by Formula 1 can be prepared by the method in which a [Ir(C^N)$_2$Cl]2 derivative is used as a starting material for providing for cyclometalating moeity, as reported by Watts group. See F. O. Garces, R. J. Watts, Inorg. Chem. 1988, (35), 2450) which is incorporated herein by reference.

The synthesis routes of iridium complexes according to various examples of the present invention will now be described.

Referring to Reaction Schemes 1-3, the [Ir(C^N)$_2$Cl]$_2$ derivative as the starting material and N containing compounds (N-compound) were mixed with a solvent such as 1,2-dichloromethane, methylene chloride, or THF, and stirred at room temperature for 2 to 48 hours, giving a [Ir(C^N)$_2$Cl]N-compound. The resulting product [Ir(C^N)$_2$Cl]N-compound was mixed with KCN, NaSCN or KOCN in a solvent such as 1,2-dichloromethane, methylene chloride, THF or methanol, and reacted at a temperature from room temperature to 50° C. for 1 to 48 hours, yielding final products [Ir(C^N)$_2$SCN]N-compound, [Ir(C^N)$_2$CN]N-compound, or [Ir(C^N)$_2$OCN]N-compound, in which Cl bonded to iridium is substituted by CN, SCN, and OCN, respectively.

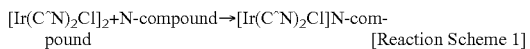
[Reaction Scheme 1]

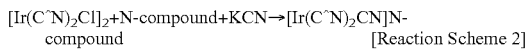
[Reaction Scheme 2]

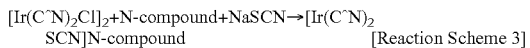
[Reaction Scheme 3]

[Reaction Scheme 4]

wherein the cyclometalating ligand and the N-compounds are as defined as above.

The organic electroluminescent device according to the present invention is manufactured by forming an organic layer, particularly a light-emitting layer, using the organometallic complex represented by Formula 1. The organometallic complex represented by Formula 1 is very advantageously used as a phospholuminescent dopant material, which is a material for forming the light-emitting layer, and exhibits an excellent emission efficiency in the blue range.

When the organometallic complex represented by Formula 1 is used as a 23 phospholuminescent dopant, the organic layer may further comprises at least one selected 24 from the group consisting of at least one polymer host, a mixture of a polymer host and a small molecular host, a small molecular host, and non-luminous polymer matrix. Any useful materials known in the art as materials for forming a light-emitting layer of an organic electroluminescent device can be used for the polymer host, the small molecular host and the non-luminous polymer matrix. Typical examples of the polymer host include, but are not limited to, poly(vinylcarbazole) (PVK), polyfluorene and the like. Typical examples of the small molecular host include, but are not limited to, CBP(4, 4'-N,N'-dicarbazole-biphenyl), 4,4'-bis[9-(3,6-biphenylcarbazollyl)]-1-1,1'-biphenyl {4,4'-bis[9-(3,6-biphenylcarbazollyl)]-1-1,1'-biphenyl}, 9,10-bis[(2',7'-t-butyl)-9',9"-spirobifluorenylanthracene, tetrafluorene and the like. Typical examples of the non-luminous polymer matrix include, but are not limited to, polymethacrylate, polystyrene and the like.

Preferably, the organometallic complex represented by Formula 1 is contained in an amount of about 1 to 30 parts by weight based on the total weight of the light-emitting layer forming material. Examples of methods useful to introduce the organometallic complex to the light-emitting layer include vacuum deposition, sputtering, printing, coating, ink-jet printing, electron-beam application, and so on.

The organometallic complex represented by Formula 1 can induce white electroluminescence when combined with green or red luminescent materials.

The thickness of the organic layer is preferably in a range of about 30 to 100 mm. The term "organic layer" used herein means a layer made of an organic compound formed between a pair of electrodes in an organic electroluminescent device, for example, a h light-emitting layer, an electron transport layer, a hole transport layer, and the like. The organic electroluminescent device may have a known structure selected from the group consisting of anode/light-emitting layer/cathode, anode/buffer layer/light-emitting layer/cathode, anode/hole transport layer/light-emitting layer/cathode, anode/buffer layer/hole transport layer/light-emitting layer/cathode, anode/buffer layer/hole transport layer/light-emitting layer/electron transport layer/cathode, and anode/buffer layer/hole transport layer/light-emitting layer/hole blocking layer/cathode, but is not particularly limited to these structures.

Examples of the buffer layer include any materials commonly used in the art. Preferably, copper phthalocyanine, polythiophene, polyaniline, polyacetylene, polypyrrole, polyphenylene vinylene, and derivatives thereof can be used for the buffer layer.

Examples of the hole transport layer include any materials commonly used in the art. Preferably, the hole transport layer includes polytriphenylamine.

Examples of the electron transport layer include any materials commonly used in the art. Preferably, the electron transport layer includes polyoxadiazole.

Examples of the hole blocking layer include any materials commonly used in the art. Preferably, the hole blocking layer includes LiF, $BaF_2$ or $MgF_2$.

The organic electroluminescence device according to the present invention can be manufactured in accordance with conventional apparatus and methods in the art without any limitations.

The iridium complex can emit light of wavelengths in a range from 400 to 650 nm. Light emitting diodes (or light emitting devices, LEDs) using such organometallic complexes can be used in applications such as light sources for a full color display, backlighting, signboards, optical communication, indoor decoration, and the like.

Hereinafter, the present invention will now be described in more detail with reference to the following Examples. However, these examples are given for the purpose of illustration and not of limitation.

Reference Example 1

Synthesis of $F_2$PPY Dimer

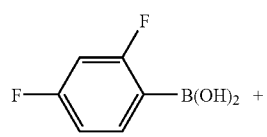
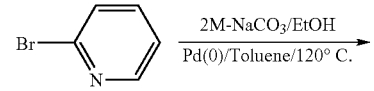
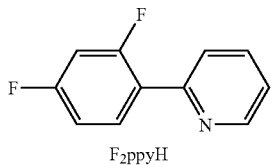
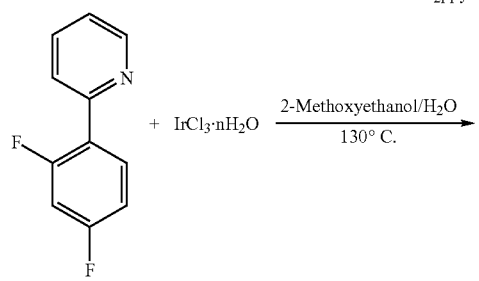
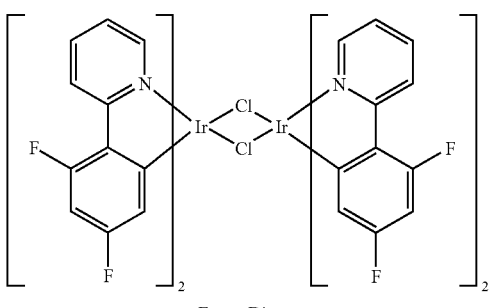

A 2M sodium carbonate solution prepared by mixing 19.85 g ($1.25 \times 10^4$ mmol) of 2-bromopyridine, 25.00 g ($1.58 \times 10^4$ mol) of 2,4-difluorophenyl boronic acid, 100 mL of toluene, 48 mL of ethanol and 95 mL of water was placed in a 500 mL flask, and stirred under a nitrogen atmosphere at room temperature. Then, to the sodium carbonate solution was added 4.53 g (3.92 mmol) of tetrakis(triphenylphosphine) palladium(0) and refluxed for 15 hours under a nitrogen atmosphere while the reaction was kept in dark.

After the reaction was completed, the temperature of the reaction mixture was adjusted to room temperature, followed by extracting using ethyl acetate and water and separating the extract by column chromatography with 10:1 toluene/hexane, giving a light brown liquid ($F_2$ ppyH). The product was identified through $^1$H-NMR spectroscopy. $^1$H-NMR ($CD_2Cl_2$, ppm): 8.69 [d, 1H], 8.03 [m, 1H], 7.70 [m, 2H], 7.27 [m, 1H], 7.00 [m, 2H].

A single substance of the synthesized product 2-(4,6-difluorophenylpyridine), and IrC13.nH2O were used to prepare a $F_2$ppy dimer as a yellow powder. The preparation method described in J. Am. Che. Soc., 1984, 106, 6647-6653 was incorporated herein by reference. The product was identified through $^1$H-NMR spectroscopy. $^1$H-NMR ($CD_2Cl_2$, ppm): 9.1 [d, 4H], 8.3 [d, 4H], 7.9 [t, 4H], 6.9 [m, 4H], 6.5 [m, 4H], 5.3 [d, 4H].

Reference Example 2

Synthesis of $F_2$PMP Dimer

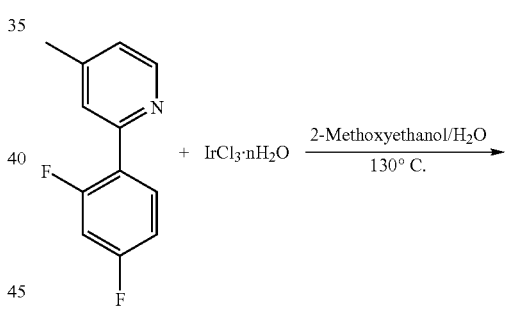
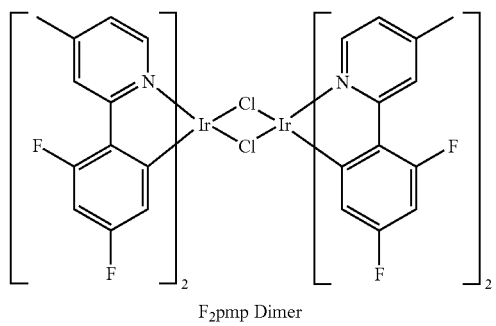

A $F_2$ pmp dimer was synthesized by the same method as in Reference Example 1, except that 2-bromo-4-methylpyridine rather than 2-bromopyridine is used.

$^1$H-NMR (CD$_2$Cl$_2$, ppm): 8.9 [d, 4H], 8.1 [s, 4H], 6.6 [d, 4H], 6.3 [m, 4H], 5.3 [d, 4H], 2.6 [s, 12H]

Reference Example 3

Synthesis of DMAF$_2$PPY Dimer

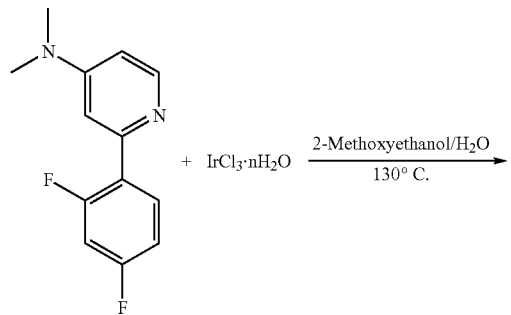

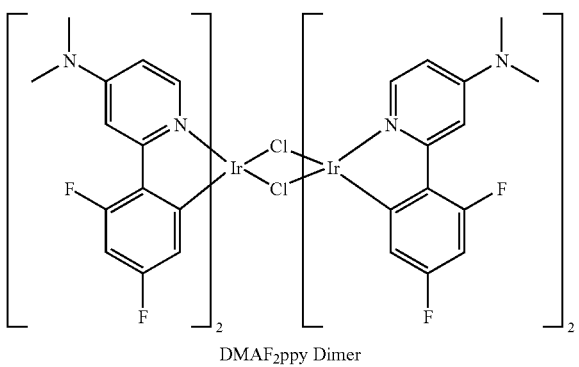

DMAF$_2$ppy Dimer

A DMAF$_2$ ppy dimer was synthesized in the same manner as in Reference EXAMPLE 1, except that 2-bromo-4-dimethylamino pyridine rather than 2-bromopyridine is used.

$^1$H-NMR (CD$_2$Cl$_2$, ppm): 8.7 [d, 4H], 7.5 [t, 4H], 6.3 [m, 4H], 6.1 [m, 4H] 5.4 [d, 4H], 3.2 [s, 24H]

Example 1

Synthesis of Compound Represented by Formula 15

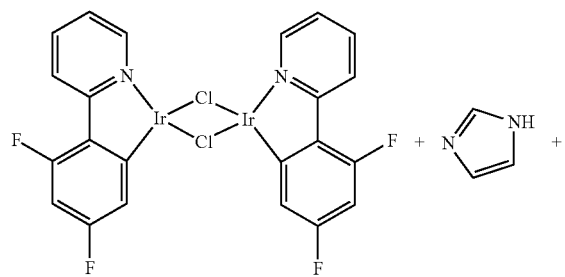

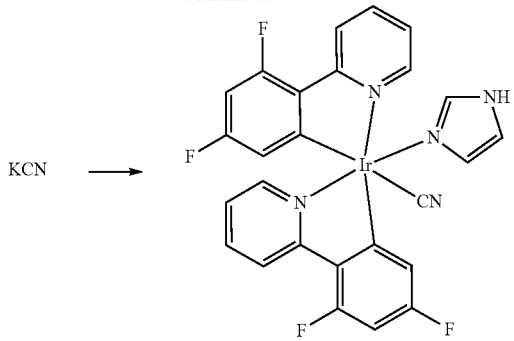

0.4 mmol of [Ir(F$_2$ ppy)$_2$Cl]$_2$, and 0.88 mmol of imidazole were placed in a 250 mL branched flask, dissolved in 50 mL of methylene chloride under a nitrogen atmosphere and reacted at room temperature for 10 hours.

After the reaction was completed, the reaction mixture was passed through a pad of celite for filtration, followed by precipitating in hexane, giving [Ir(F$_2$ ppy)$_2$Cl]$_2$-[2imidazole] as a yellow powder. 0.5 mmol of [Ir(F$_2$ ppy)$_2$Cl]$_2$-[2imidazole] was dissolved in 20 ml methylene chloride in a reactor, 2.5 mmol potassium cyanide dissolved in 15 ml methanol was added thereto, and stirred at room temperature for 16 hours. After the reaction was completed, the reaction solution was filtered by passing through a pad of celite and the filtrate was precipitated in hexane, acquiring a yellow solid. The acquired yellow solid was purified by a silica gel column using a mixed solvent consisting of methylene chloride and acetone in a volume ratio of 10:1. The product was identified through $^1$H-NMR spectroscopy. $^1$H-NMR (CD$_2$Cl$_2$, ppm): 9.7 [d, 1H], 8.3-8.4 [m, 2H], 8.2 [d, 1H], 8.0 [d, 1H], 7.8-7.9 [q, 2H], 7.2 [t, 1H], 7.1 [t, 1H], 6.9 [s, 1H], 6.7 [s, 1H], 6.4-6.5 [m, 2H], 5.7-5.8 [m, 2H].

The obtained compounds were tested for emission characteristics in the following manners.

First, the compound represented by Formula 15 was dissolved in methylene chloride to prepare a 10$^{-4}$ M solution, and then emission characteristics of the compound being in a solution state were evaluated. Next, 94 parts by weight of polymethylmethacrylate (PMMA) and 6 parts by weight of the compound represented by Formula 15 were dissolved in 1,2-dichloroethane or chlorobenzene and spin-coated to then be fabricated into a film. Then, the emission characteristics of the compound being in a film state were evaluated.

The results showed that the compound represented by Formula 15 had an emission wavelength peak at 457.5 nm with a shoulder at 485 nm in a solution state, and that the compound had substantially the same emission profile with that in a film state.

The CIE (Commission Internationale de l'Eclairage) color coordinate (x, y) of the compound was (0.145, 0.20).

Example 2

Synthesis of Compound Represented by Formula 16

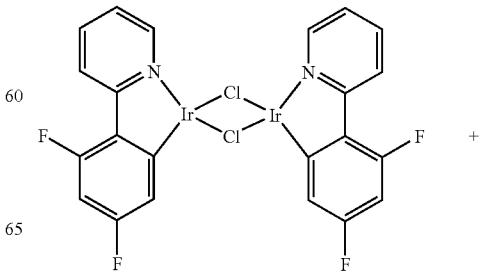

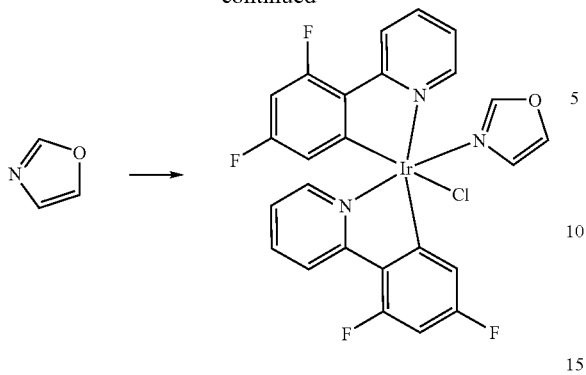

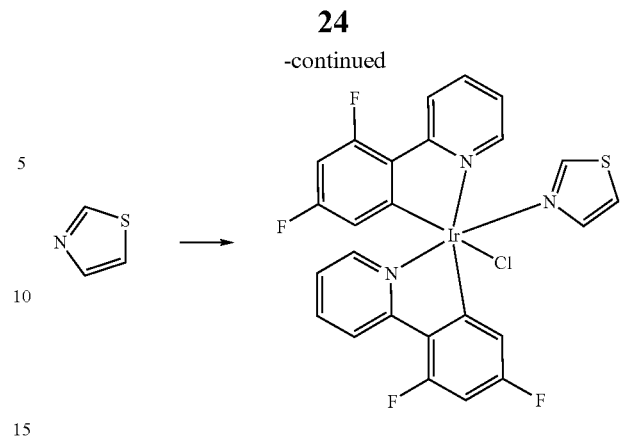

0.4 mmol of [Ir(F₂ ppy)₂Cl]₂, and 0.88 mmol of oxazole were placed in a 250 mL branched flask, dissolved in 50 mL methylene chloride under a nitrogen atmosphere and reacted at room temperature for 10 hours.

After the reaction is completed, the reaction mixture was passed through a pad of celite for filtration, followed by precipitating in hexane, giving [Ir(F₂ ppy)₂Cl]₂-[2oxazole] as a yellow powder. The acquired yellow solid was purified by silica gel column using a mixed solvent consisting of methylene chloride and hexane in a volume ratio of 10:1. The product was identified through ¹H-NMR spectroscopy. ¹H-NMR (CD₂Cl₂, ppm): 9.8 [d, 1H], 8.6 [s, 1H], 8.3 [d, 1H], 8.2 [d, 1H], 8.1 [d, 1H], 7.8-7.9 [m, 2H], 7.7 [s, 1H], 7.3 [t, 1H], 7.2 [s, 1H], 7.1 [t, 1H], 6.3-6.5 [m, 2H], 5.8 [d, 1H], 5.6 [d, 1H].

The obtained compounds were tested for emission characteristics in the following manner. In other words, the compound represented by Formula 16 was dissolved in methylene chloride to prepare a 10⁻⁴ M solution, and then emission characteristics of the compound being in a solution state were evaluated. The results showed that the compound represented by Formula 16 had an emission wavelength peak at 468.6 nm with a shoulder at 492.6 nm in a solution state.

The CIE color coordinate (x, y) of the compound was (0.1431, 0.2675).

The desired product was synthesized in the same manner as in EXAMPLE 2, except that thiazole, rather than oxazole, was used, and the product was identified through ¹H-NMR spectroscopy. ¹H-NMR (CD₂Cl₂, ppm): 9.9 [d, 1H], 9.5 [s, 1H], 8.3 [d, 1H], 8.2 [d, 1H], 7.7-7.9 [m, 4H], 7.4 [t, 1H], 7.2-7.3 [t, 1H], 7.1 [t, 1H], 6.3-6.5 [m, 2H], 5.8-5.9 [d, 1H], 5.6 [d, 1H].

The obtained compound represented by Formula 17 were tested for emission characteristics in the same manner as in Example 2. The results showed that the compound represented by Formula 17 had an emission wavelength peak at 470.2 nm with a shoulder at 492.6 nm in a solution state.

The CIE color coordinate (x, y) of the compound was (0.1436, 0.2852).

Example 4

Synthesis of Compound Represented by Formula 18

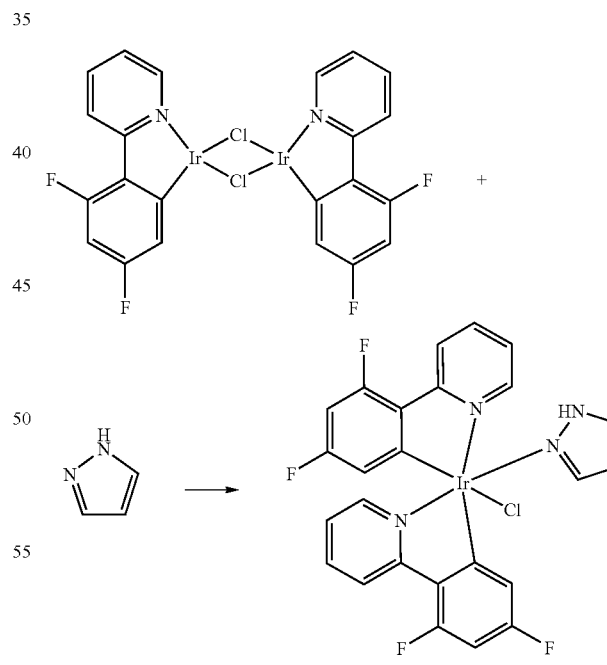

Example 3

Synthesis of Compound Represented by Formula 17

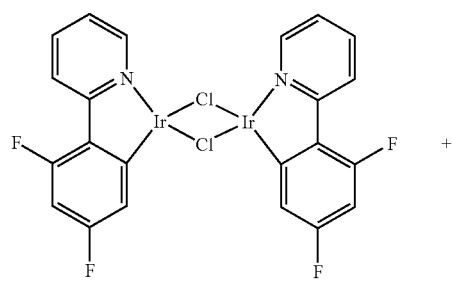

The desired product was synthesized in the same manner as in Example 2, except that pyrazole, rather than oxazole, was used, and the product was identified through ¹H-NMR spectroscopy. ¹H-NMR (CD₂Cl₂, ppm): 12.0 [s, 1H], 9.7 [d, 1H], 8.3 [d, 1H], 8.2 [d, 1H], 7.8-7.9 [m, 2H], 7.6-7.7 [m, 2H], 7.2-7.3 [t, 1H], 7.1 [t, 1H], 6.78 [s, 1H], 6.3-6.5 [m, 2H], 6.27 [m, 1H], 5.8 [d, 1H], 5.65 [d, 1H].

The obtained compound represented by Formula 18 were tested for emission characteristics in the same manner as in Example 2. The results showed that the compound represented by Formula 17 had an emission wavelength peak at 467.3 nm with a shoulder at 492.6 nm in a solution state.

The CIE color coordinate (x, y) of the compound was (0.1418, 0.2064).

Example 5

Synthesis of Compound Represented by Formula 19

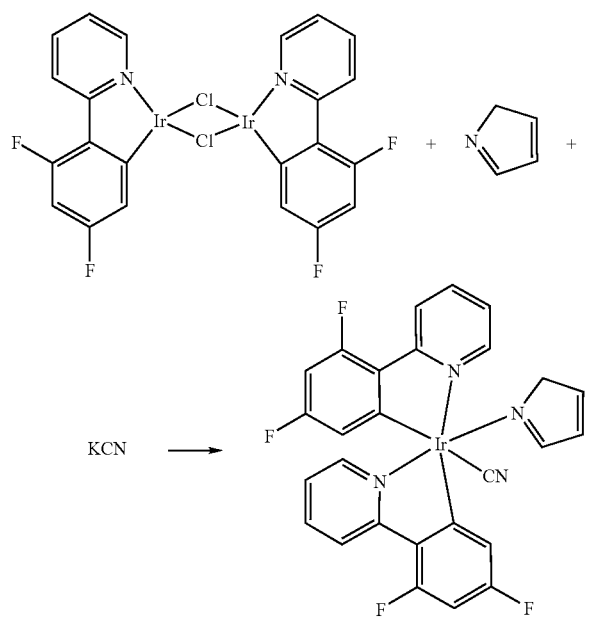

The desired product was synthesized in the same manner as in Example 1, except that 2H-pyrrole, rather than imidazole, was used, and the product was identified through $^1$H-NMR spectroscopy. The emission characteristics of the obtained compound were evaluated by the same method as that for the compound represented by Formula 16.

Example 6

Synthesis of Compound Represented by Formula 20

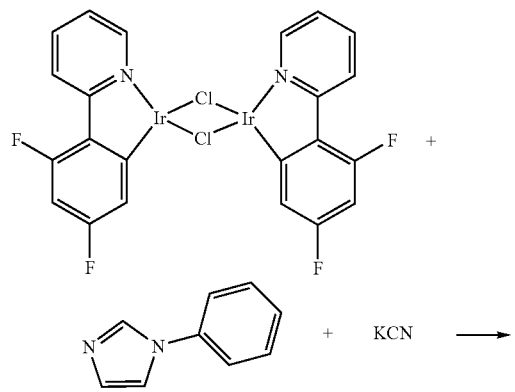

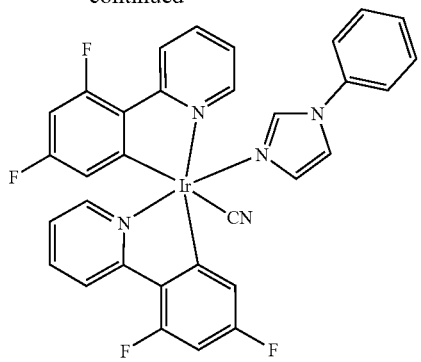

The desired product was synthesized in the same manner as in Example 1, except that 1-phenylimidazole, rather than imidazole, was used, and the product was identified through $^1$H-NMR spectroscopy. $^1$H-NMR (CD$_2$Cl$_2$, ppm): 9.8 [d, 1H], 8.3-8.4 [d, 2H], 8.2-8.3 [d, 1H], 8.1-8.2 [d, 1H], 7.8-7.9 [q, 2H], 7.3-7.6 [m, 5H], 7.2-7.3 [m, 2H], 7.12 [t, 1H], 7.03 [s, 1H], 6.4-6.5 [m, 2H], 5.78 [m, 2H].

The emission characteristics of the obtained compound were evaluated by the same method as that for the compound prepared in Example 1. The results showed that the compound represented by Formula 20 had an emission wavelength peak at 457.2 nm with a shoulder at 484.7 nm in a solution state and an emission wavelength peak at 456.5 nm with a shoulder at 484 nm in a film state. That is, the film PL is blue-shifted by approximately 1 nm from the solution PL.

The CIE color coordinate (x, y) of the compound was (0.147, 0.195).

Example 7

Synthesis of Compound Represented by Formula 33

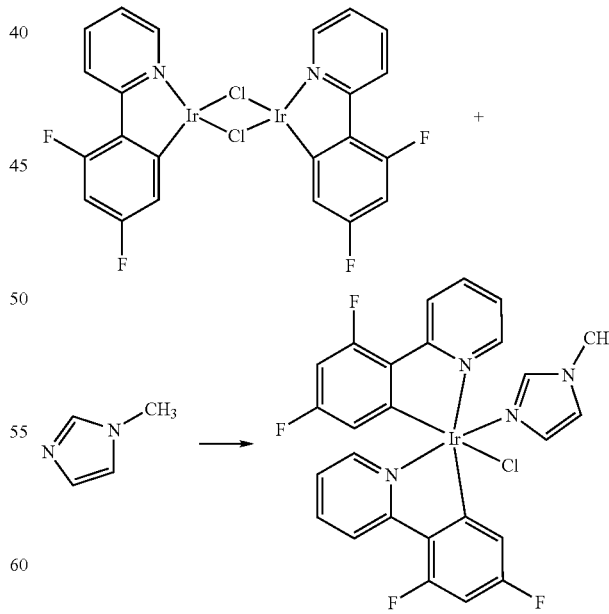

The desired product was synthesized in the same manner as in Example 2, except that (1-methyl)imidazole, rather than oxazole, was used, and the product was identified through $^1$H-NMR spectroscopy. $^1$H-NMR (CD$_2$Cl$_2$, ppm): 9.8 [d, 1H], 8.3 [d, 1H], 8.1 [m, 3H], 7.7 [m, 2H], 7.2 [t, 1H], 7.1 [t, 1H], 6.78 [s, 1H], 6.75 [s, 1H], 6.3-6.5 [m, 2H], 5.8 [d-d, 1H], 5.6 [d-d, 1H], 3.6 [s, 3H].

The emission characteristics of the obtained compound were evaluated by the same method as that for the compound represented by Formula 16. The results showed that the compound had an emission wavelength at 473.8 nm in a solution state.

The CIE color coordinate (x, y) of the compound was (0.1451, 0.3249).

Example 8

Synthesis of Compound Represented by Formula 34

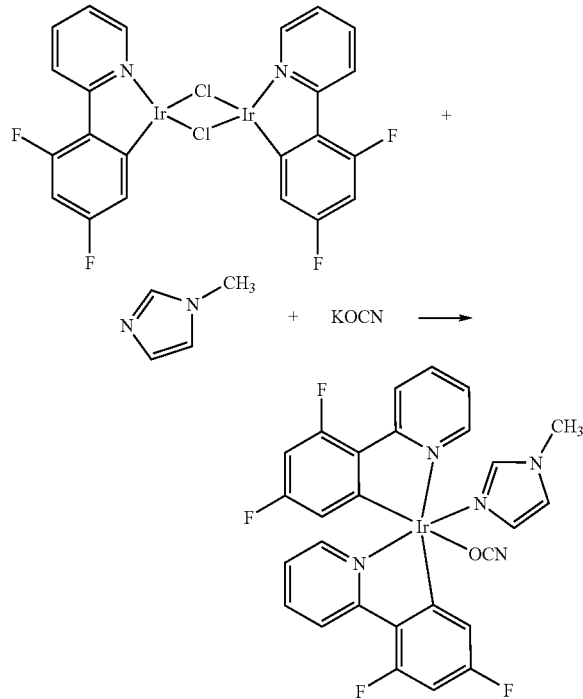

The desired product was synthesized in the same manner as in Example 1, except that (1-methyl)imidazole and KOCN were used instead of imidazole and KCN, respectively, and the product was identified through $^1$H-NMR spectroscopy.
$^1$H-NMR (CD$_2$Cl$_2$, ppm): 9.36 [d, 1H], 8.3 [d, 1H], 8.2 [d, 1H], 8.0 [d, 1H], 7.8 [m, 2H], 7.7 [s, 1H], 7.2 [t, 1H], 7.1 [t, 1H], 6.81 [s, 1H], 6.79 [s, 1H], 6.4 [m, 2H], 5.8 [d-d, 1H], 5.6 [d-d, 1H], 3.6 [s, 3H].

The emission characteristics of the obtained compound were evaluated by the same method as that for the compound prepared in Example 1. The results showed that the compound had an emission wavelength at 473.8 nm in a solution state. The CIE color coordinate (x, y) of the compound was (0.1457, 0.3205).

Example 9

Synthesis of Compound Represented by Formula 35

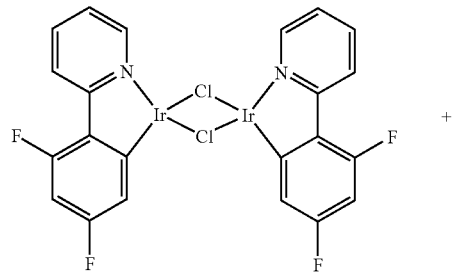

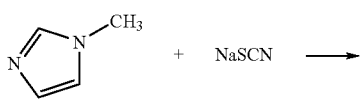

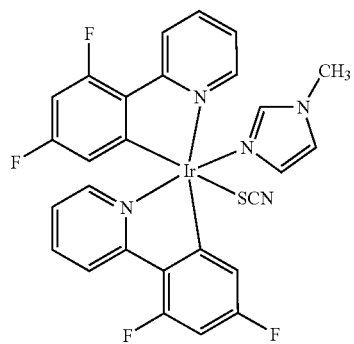

The desired product was synthesized in the same manner as in Example 1, except that (1-methyl)imidazole and NaSCN were used instead of imidazole and KCN, respectively, and the product was identified through $^1$H-NMR spectroscopy.
$^1$H-NMR (CD$_2$Cl$_2$, ppm): 9.2 [d, 1H], 8.3 [d, 1H], 8.2 [d, 1H], 8.0 [d, 1H], 7.8 [m, 2H], 7.5 [s, 1H], 7.3 [t, 1H], 7.1 [t, 1H], 6.85 [s, 1H], 6.8 [s, 1H], 6.4 [m, 2H], 5.65 [d-d, 2H], 3.6 [s, 3H].

The obtained compound represented by Formula 35 were tested for emission characteristics in the same manner as in Example 1. The results showed that the compound represented by Formula 17 had an emission wavelength peak at 466 nm with a shoulder at 490 nm in a solution state. The CIE color coordinate (x, y) of the compound was (0.1429, 0.2535).

Example 10

Synthesis of Compound Represented by Formula 21

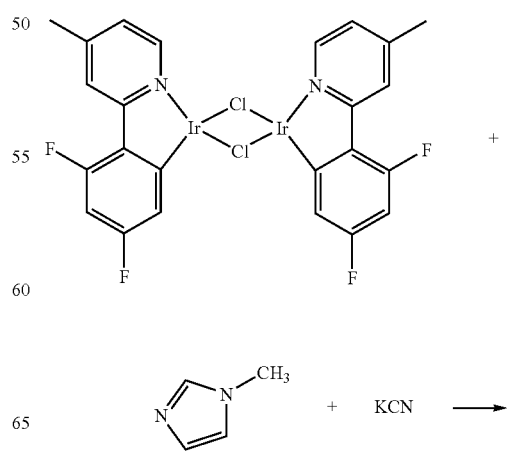

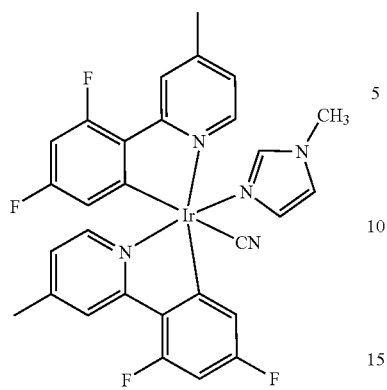

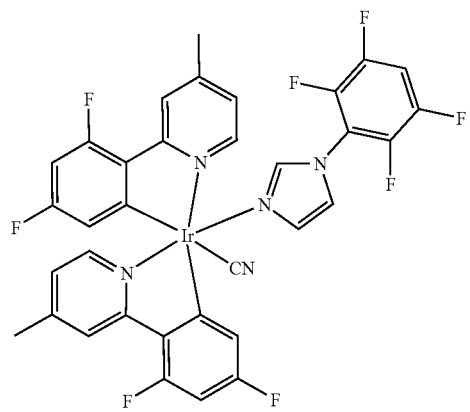

The desired product was synthesized in the same manner as in Example 1, except that a $F_2$ pmp dimer and (1-methyl) imidazole were used instead of $F_2$ ppy dimer and imidazole, respectively, and the product was identified through $^1$H-NMR spectroscopy. $^1$H-NMR (CD$_2$Cl$_2$, ppm): 9.5 [d, 1H], 8.1 [s, 1H], 8.0 [s, 1H, 7.88 (s, 1H], 7.85 [d, 1H], 7.0 [d, 1H], 6.9 [d, 1H], 6.8 [s, 1H], 6.7 [s, 1H], 6.3-6.5 [m, 2H], 5.7 [m, 2H], 3.6 [s, 3H], 2.5 [d, 6H].

The emission characteristics of the obtained compound were evaluated by the same method as that for the compound prepared in Example 1. The results showed that the compound represented by Formula 21 had an emission wavelength peak at 455.8 nm with a shoulder at 482.5 nm in a solution state and an emission wavelength peak at 455 nm with a shoulder at 481.8 nm in a film state. That is, the film PL is blue-shifted by approximately 1 nm from the solution PL.

The CIE color coordinate (x, y) of the compound was (0.147, 0.195).

The desired product was synthesized in the same manner as in Example 1, except that a $F_2$ pmp dimer and 1-tetrafluorophenylimidazole were used instead of $F_2$ ppy dimer and imidazole, respectively, and the product was identified through $^1$H-NMR spectroscopy. $^1$H-NMR (CD$_2$Cl$_2$, ppm): 9.5 [d, 1H], 8.1 [s, 1H], 8.0 [s, 1H], 7.88 [s, 1H], 7.85 [d, 1H], 7.0 [d, 1H], 6.9 [d, 1H], 6.8 [s, 1H], 6.7 [s, 1H], 6.3-6.5 [m, 2H], 5.7 [m, 2H], 3.6 [s, 3H], 2.5 [d, 6H].

The emission characteristics of the obtained compound were evaluated by the same method as that for the compound represented by Formula 15 prepared in Example 1. The results showed that the compound represented by Formula 22 had an emission wavelength peak at 455.8 nm with a shoulder at 482.5 nm in a solution state and an emission wavelength peak at 455 nm with a shoulder at 481.8 nm in a film state. That is, the film PL is blue-shifted by approximately 1 nm from the solution PL.

Example 11

Synthesis of Compound Represented by Formula 22

Example 12

Synthesis of Compound Represented by Formula 23

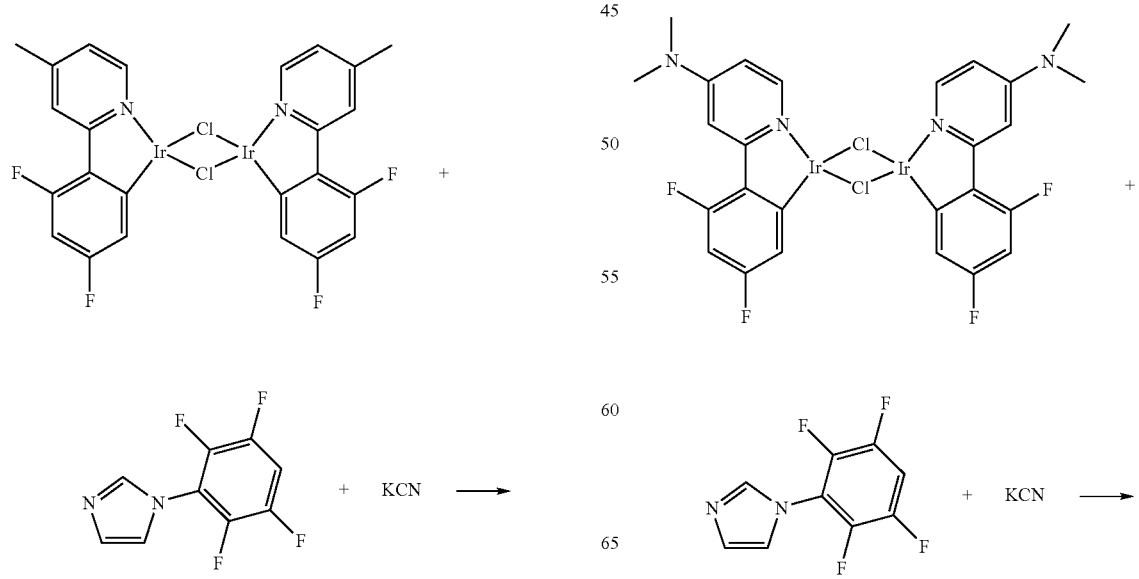

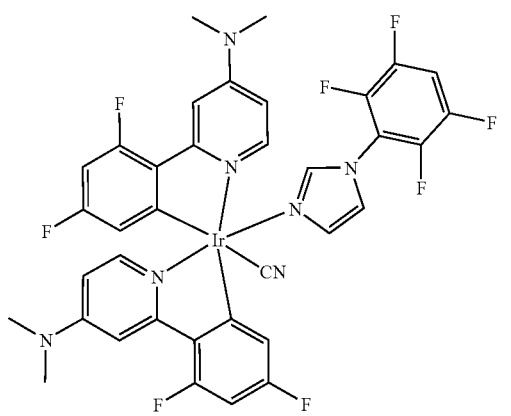

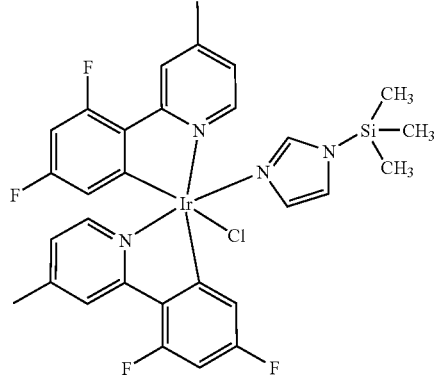

The desired product was synthesized in the same manner as in Example 1, except that a $DMNF_2$ ppy dimer and 1-tetrafluorophenylimidazole were used instead of $F_2$ ppy dimer and imidazole, respectively, and the product was identified through $^1$H-NMR spectroscopy. $^1$H-NMR ($CD_2Cl_2$, ppm): 9.1 [d, 1H], 8.2 [s, 1H], 7.6 [d, 1H], 7.5 [t, 1H], 7.4 [t, 1H], 7.2-7.3 [m, 1H], 7.2 [s, 1H], 7.1 [s, 1H], 6.3-6.5 [m, 4H], 5.8-6.0 [m, 2H], 3.1-3.2 [d, 12H].

The emission characteristics of the obtained compound were evaluated by the same method as that for the compound represented by Formula 15 prepared in Example 1. The results showed that the compound represented by Formula 0.23 had emission wavelength peaks at 446 nm and 465 nm in a solution state and emission wavelength peaks at 445 nm and 464 nm in a film state. That is, the film PL is blue-shifted by approximately 1 nm from the solution PL. The CIE color coordinate (x, y) of the compound was (0.147, 0.130).

The desired product was synthesized in the same manner as in Example 2, except that a $F_2$ pmp dimer and 1-(trimethylsilyl)imidazole were used instead of $F_2$ ppy dimer and oxazole, respectively, and the product was identified through $^1$H-NMR spectroscopy. $^1$H-NMR ($CD_2Cl_2$, ppm): 9.6 [d, 1H], 8.2 [s, 1H], 8.1 [s, 1H], 8.0 [s, 1H], 7.85 [d, 1H], 7.05 [d, 1H], 6.9 [m, 2H], 6.85 [s, 1H], 6.3-6.5 [m, 2H], 5.85 [d, 1H], 5.65 [d, 1H], 2.55 [d, 6H], 0.08 [m, 9H].

The emission characteristics of the obtained compound were evaluated by the same method as that for the compound represented by Formula 16. The results showed that the compound represented by Formula 24 had an emission wavelength peak at 469.5 nm with a shoulder at 492 nm in a solution state. The CIE color coordinate (x, y) of the compound was (0.1451, 0.2867).

Example 13

Synthesis of Compound Represented by Formula 24

Example 14

Synthesis of Compound Represented by Formula 25

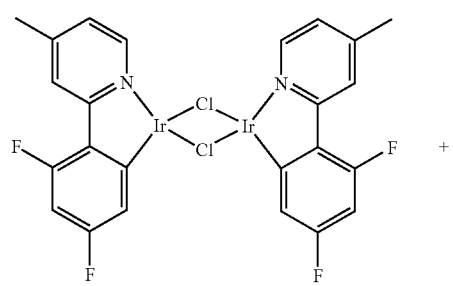

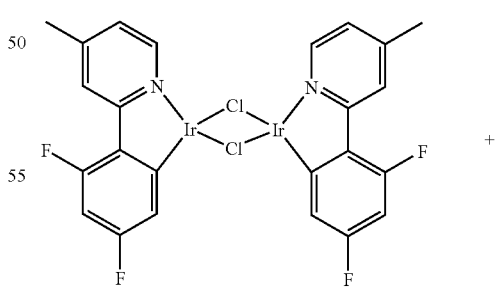

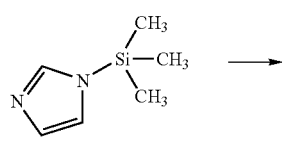

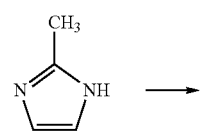

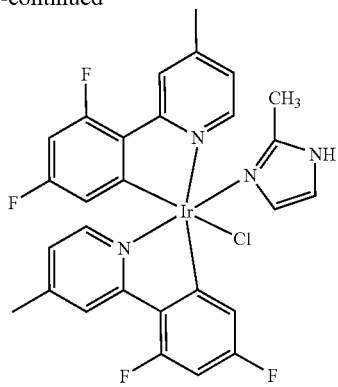

The desired product was synthesized in the same manner as in Example 2, except that a F2 pmp dimer and 2-methylimidazole were used instead of F$_2$ ppy dimer and oxazole, respectively, and the product was identified through $^1$H-NMR spectroscopy. $^1$H-NMR (CD$_2$Cl$_2$, ppm): 9.7 [d, 1H], 8.47 [d, 1H], 8.1 [s, 1H], 8.0 [s, 1H], 7.1 [d, 1H], 7.0 [d, 1H], 6.3-6.4 [m, 2H], 5.8 [d, 1H], 5.7 [d, 1H], 5.35 [s, 1H], 4.8 [s, 1H], 3.1-3.4 [m, 3H], 2.6 [d, 61H].

The emission characteristics of the obtained compound were evaluated by the same method as that for the compound represented by Formula 16. The results showed that the compound represented by Formula 25 had an emission wavelength peak at 477 nm in a solution state.

The CIE color coordinate (x, y) of the compound was (0.1544, 0.3633).

Example 15

Synthesis of Compound Represented by Formula 26

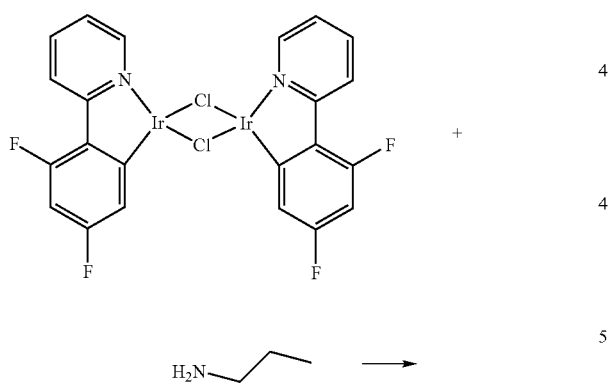

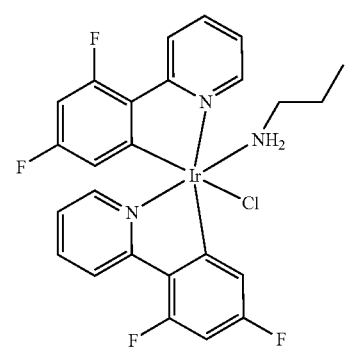

The desired product was synthesized in the same manner as in Example 2, except that propylamine was used instead oxazole, and the product was identified through $^1$H-NMR spectroscopy. $^1$H-NMR (CD$_2$Cl$_2$, ppm): 9.8 [d, 1H], 8.43 [d, 1H], 8.3 [q, 2H], 7.9 [t, 2H], 7.35 [m, 2H], 6.4 [m, 2H], 5.75 [d, 1H], 5.55 [d, 1H], 2.9 [m, 2H], 2.0-2.1 [m, 2H], 1.3 [m, 2H], 0.7 [t, 3H].

The emission characteristics of the obtained compound were evaluated by the same method as that for the compound represented by Formula 16. The results showed that the compound had an emission wavelength at 475.3 nm in a solution state.

The CIE color coordinate (x, y) of the compound was (0.1448, 0.3185).

Example 16

Synthesis of Compound Represented by Formula 27

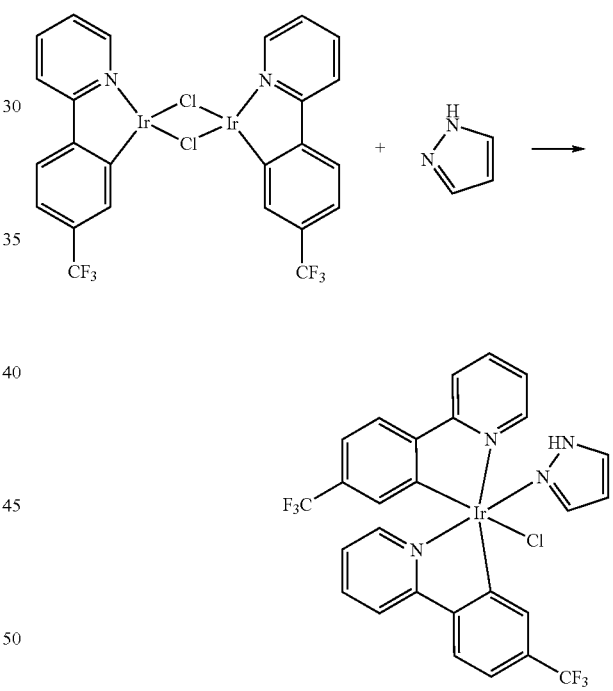

The desired product was synthesized in the same manner as in Example 2, except that a CF$_3$ ppy dimer and pyrazole were used instead of F$_2$ ppy dimer and oxazole, respectively, and the product was identified through $^1$H-NMR spectroscopy. $^1$H-NMR (CD$_2$Cl$_2$, ppm): 10.8 [s, 1H], 9.9 [d, 1H], 8.1-8.2 [d-d, 2H], 7.7-7.9 [m, 6H], 7.36 [t, 1H], 7.2 [t, 1H], 7.15 [d, 1H], 7.0 [d, 1H], 6.6 [s, 1H], 6.56 [s, 1H], 6.37 [s, 1H], 6.23 [s, 1H].

The obtained compound represented by Formula 27 were tested for emission characteristics in the same manner as in Example 16. The results showed that the compound represented by Formula 27 had an emission wavelength peak at 512 nm with a shoulder at 540 nm in a solution state.

The CIE color coordinate (x, y) of the compound was (0.2745, 0.6323).

Example 17

Synthesis of Compound Represented by Formula 28

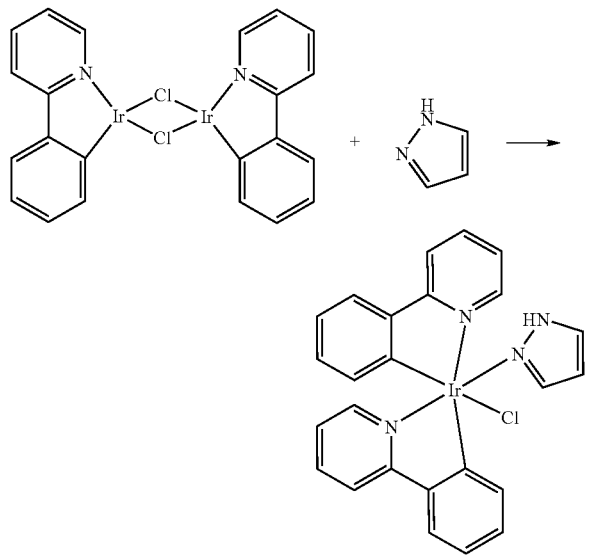

The desired product was synthesized in the same manner as in Example 2, except that a ppy dimer and pyrazole were used instead of $F_2$ ppy dimer and oxazole, respectively, and the product was identified through $^1$H-NMR spectroscopy. $^1$H-NMR (CD$_2$Cl$_2$, ppm): 10.8 [s, 1H], 9.86 [d, 1H], 7.9-8.1 [d-d, 2H], 7.5-7.75 [m, 6H], 7.17 [t, 1H], 7.0 [t, 1H], 6.81 [t, 1H], 6.5-6.7 [m, 4H], 6.4 [d, 1H], 6.1-6.3 [m, 2H].

The obtained compound represented by Formula 28 were tested for emission characteristics in the same manner as in Example 16. The results showed that the compound represented by Formula 28 had an emission wavelength peak at 500 nm with a shoulder at 530 nm in a solution state.

The CIE color coordinate (x, y) of the compound was (0.2346, 0.6183).

Example 18

Synthesis of Compound Represented by Formula 29

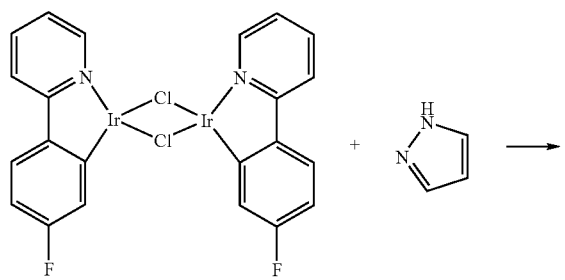

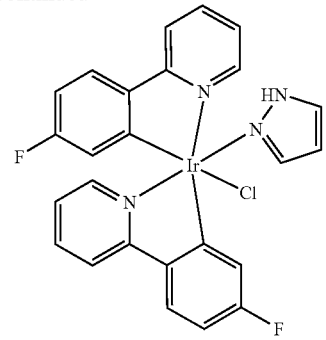

The desired product was synthesized in the same manner as in Example 2, except that a Fppy dimer and pyrazole were used instead of $F_2$ ppy dimer and oxazole, respectively, and the product was identified through $^1$H-NMR spectroscopy the product was identified through $^1$H-NMR spectroscopy. $^1$H-NMR(CD$_2$Cl$_2$, ppm): 10.8 [s, 1H], 9.8 [d, 1H], 7.6-8.0 [m, 8H], 7.2 [t, 1H], 7.0 [t, 1H], 6.7 [s, 1H], 6.6 [m, 1H], 6.47 [m, 1H], 6.2 [s, 1H], 5.93 [d-d, 1H], 5.75 [d-d, 1H].

The obtained compound represented by Formula 29 were tested for emission characteristics in the same manner as in Example 16. The results showed that the compound represented by Formula 29 had an emission wavelength peak at 482.5 nm with a shoulder at 513.5 nm in a solution state.

The CIE color coordinate (x, y) of the compound was (0.1657, 0.4439).

Example 19

Synthesis of Compound Represented by Formula 30

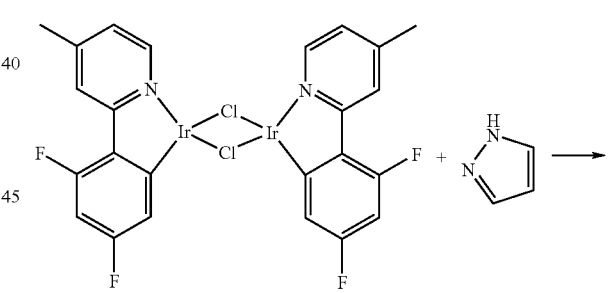

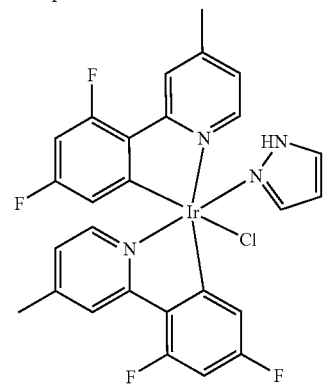

The desired product was synthesized in the same manner as in Example 2, except that a $F_2$ pmp dimer and pyrazole were used instead of $F_2$ ppy dimer and oxazole, respectively, and the product was identified through $^1$H-NMR spectroscopy. $^1$H-NMR (CD$_2$Cl$_2$, ppm): 10.8 [s, 1H], 9.66 [d, 1H], 8.1 [s, 1H], 8.0 [s, 1H], 7.77 [s, 1H], 7.55 [d, 1H], 7.13 [d, 1H], 6.96 [d, 1H], 6.7 [s, 1H], 6.5 [m, 1H], 6.4 [m, 1H], 6.25 [s, 1H], 5.8 [d-d, 1H], 5.6 [d-d, 1H], 2.55 [d, 6H].

The obtained compound represented by Formula 30 were tested for emission characteristics in the same manner as in Example 16. The results showed that the compound represented by Formula 30 had an emission wavelength peak at 468 nm with a shoulder at 490 nm in a solution state.

The CIE color coordinate (x, y) of the compound was (0.1443, 0.2669).

Example 20

Synthesis of Compound Represented by Formula 31

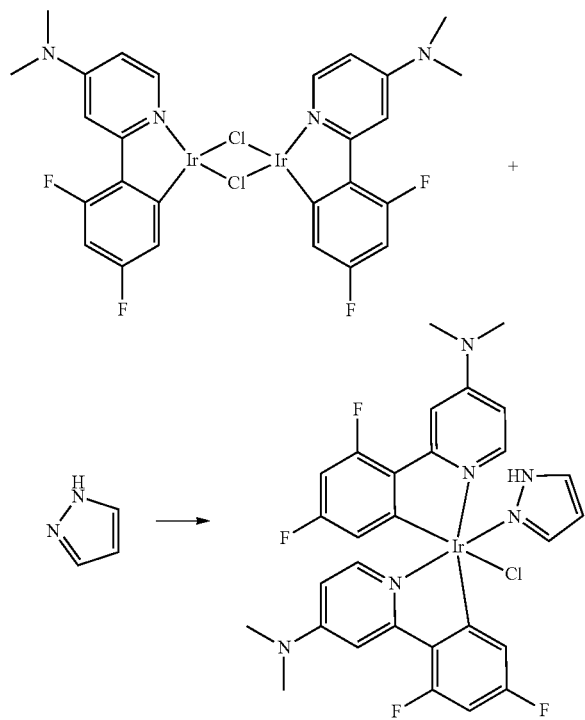

The desired product was synthesized in the same manner as in Example 2, except that DMN2Fppy dimer and pyrazole were used instead of F$_2$ ppy dimer and oxazole, respectively, and the product was identified through $^1$H-NMR spectroscopy. $^1$H-NMR (CD$_2$Cl$_2$, ppm): 10.8 [s, 1H], 9.25 [d, 1H], 7.74 [s, 1H], 7.48 [t, 1H], 7.42 [t, 1H], 718 [d, 1H], 6.7 [s, 1H], 6.56 [d-d, 1H], 6.39-6.42 [m, 2H], 6.20-6.24 [m, 2H], 5.93 [d-d, 1H], 5.74 [d-d, 1H], 3.1 [d, 12H].

The obtained compound represented by Formula 31 were tested for emission characteristics in the same manner as in Example 16. The results showed that the compound represented by Formula 31 had an emission wavelength peak at 458 nm with a shoulder at 480 nm in a solution state.

The CIE color coordinate (x, y) of the compound was (0.1445, 0.1858).

FIGS. 1 through 5 illustrate emission characteristics of the organometallic complexes prepared in various examples of the present invention.

Figure 2:
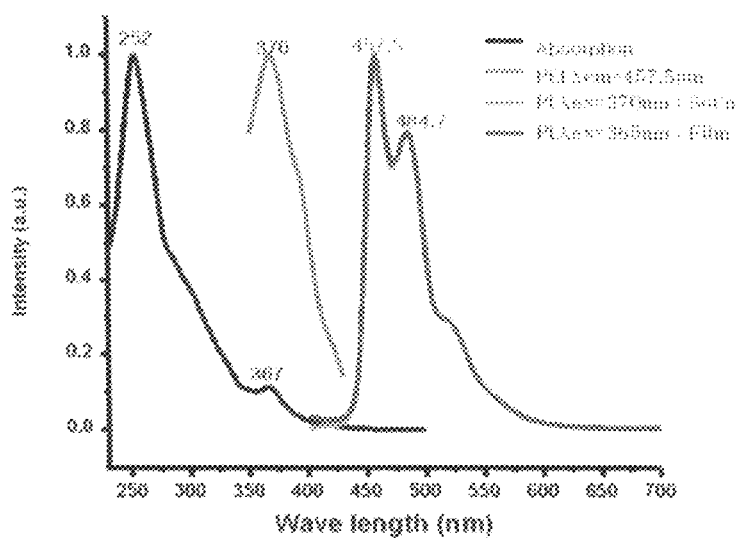
FIG. 2 shows an ultraviolet (UV)-absorption spectrum of a compound represented by Formula 15 and PL spectra of a solution and a film prepared therefrom.
Figure 3:
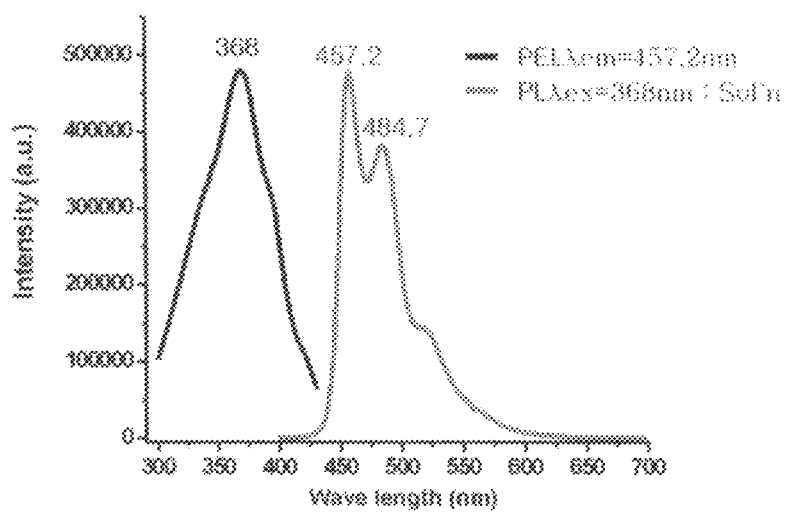
FIG. 3 shows an UV-absorption spectrum and a PL spectrum of a compound represented by Formula 20.
Figure 4:
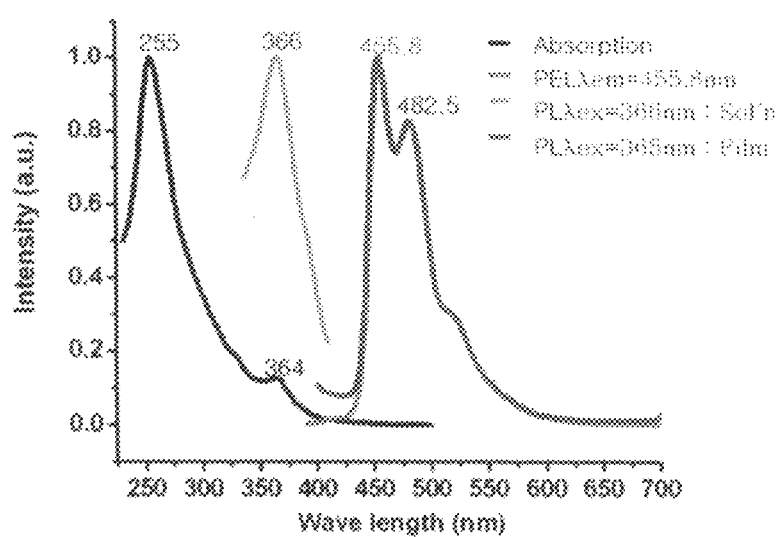
FIG. 4 shows an UV-absorption spectrum of a compound represented by Formula 21 and PL spectra of a solution and a film prepared therefrom.
Figure 5:
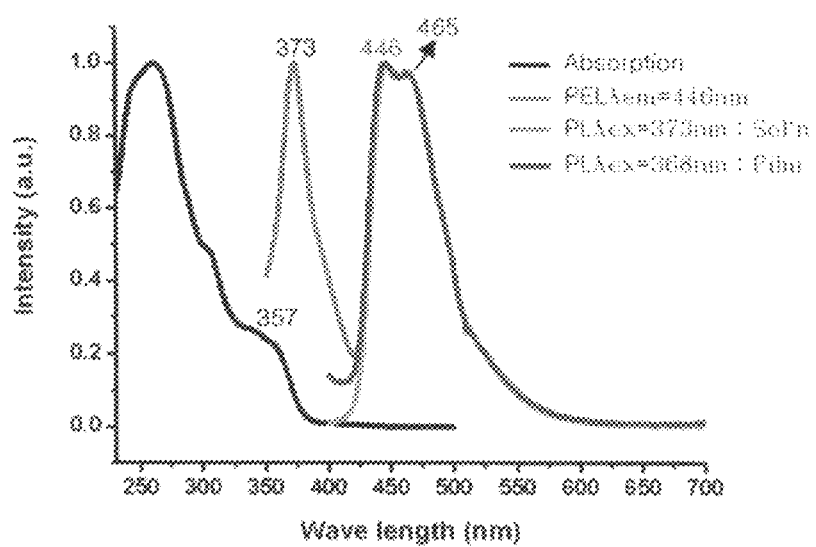
FIG. 5 shows an UV-absorption spectrum of a compound represented by Formula 22 and PL spectra of a solution and a film prepared therefrom.

FIG. 1 shows photoemission (PL) spectra of compounds represented by Formulas 32 and 16 through 18. FIG. 2 shows an ultraviolet (UV)-absorption spectrum and PL spectra of a compound represented by Formula 15. FIG. 3 shows an UV-absorption spectrum and a PL spectrum of a compound represented by Formula 20. FIG. 4 shows an UV-absorption spectrum and PL spectra of a compound represented by Formula 21, and FIG. 5 shows an UV-absorption spectrum and PL spectra of a compound represented by Formula 22.

The emission characteristics and the CIE color coordinate characteristics of the compounds prepared in various examples of the present invention are summarized in Tables 1 through 3. Table 1 shows emission and CIE characteristics of iridium complexes formed of [F$_2$ ppy]$_2$Ir-azole compounds, Table 2 shows emission and CIE characteristics of iridium complexes formed of imidazole derivatives, and Table 3 shows emission and CIE characteristics of iridium complexes formed of phenylpyridine(ppy) derivatives and pyrazole.

TABLE 1

| Structure | $\lambda_{max}$ nm Sol'n[a] | CIE cordinates x | y |
|---|---|---|---|
| (F$_2$ppy)$_2$Ir with imidazole | 474 | 0.146 | 0.323 |
| (F$_2$ppy)$_2$Ir with pyrazole | 472 | 0.143 | 0.305 |
| (F$_2$ppy)$_2$Ir with pyrazole | 470 | 0.144 | 0.285 |
| (F$_2$ppy)$_2$Ir with thiazole | | | 0.268 |

[a]10$^{-4}$M methylene chloride solution

TABLE 2

| Structure | λ_max nm | | CIE cordinates | |
|---|---|---|---|---|
| | Sol'n | Film | x | y |
| (structure 1) | 473.8 | 476 | 0.1456 | 0.3262 |
| (structure 2) | 457.5 | 457.5 | 0.1449 | 0.2076 |
| (structure 3) | 455.8 | 455 | 0.1470 | 0.1956 |
| (structure 4) | 446 | 445 | 0.1472 | 0.1295 | a: $10^{-4}$M methylene chloride solution
b: 5 wt % doped into polymethylmethacrylate

TABLE 3

| Structure | λ_max nm Sol'n[a] | CIE cordinates x | y |
|---|---|---|---|
| (structure) | 500 | 0.23 | 0.62 |
| (structure) | 512 | 0.27 | 0.63 |
| (structure) | 482 | 0.17 | 0.44 |
| (structure) | 472 | 0.14 | 0.30 |
| (structure) | 468 | 0.14 | 0.26 |
| (structure) | 458 | 0.14 | 0.19 |

[a] $10^{-4}$ M methylene chloride solution

From Tables 1 through 3, it was found that dopants having excellent phospholuminescence could be formed by introduction of azole compounds as ancillary ligands. In particular, introduction of the azole compounds in combination with CN has led to a strong electronic effect, allowing the dopants to be suitably used as blue phospholuminescent materials that emit light of wavelengths in a range of 440-460 nm. Also, introduction of various main ligands enables a full color display of red, green and blue lights.

The organometallic complex represented by Formula 1 can efficiently emit light of wavelengths from a blue range to a red range using triplet MLCT. The organometallic complex is suitably used for forming an organic layer of the organic electroluminescent device, and can emit light in a wavelength range of 400-650 nm. Also, it can induce white electroluminescence when combined with green or red luminescent materials.

The organometallic complex according to the present invention can be used in forming an organic layer in an organic electroluminescent device, e.g., a light-emitting layer.

While the present invention has been particularly shown and described with reference to preferred embodiments thereof, it will be understood by those of ordinary skill in the art that various changes in form and details may be made therein without departing from the spirit and scope of the present invention as defined by the following claims.

What is claimed is:

1. An organometallic complex represented by Formula 1:

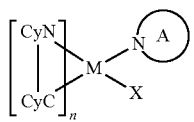

[Formula 1]

wherein M is a metal selected from the group consisting of Ir, Os, Pt, Pb, Re, Ru, and Pd;

CyN is selected from the group consisting of a substituted $C_3$-$C_{60}$ heterocyclic group containing nitrogen bonded to said M, an unsubstituted $C_3$-$C_{60}$ heterocyclic group containing nitrogen bonded to said M, a substituted $C_3$-$C_{60}$ heteroaryl group containing nitrogen bonded to said M, and an unsubstituted $C_3$-$C_{60}$ heteroaryl group containing nitrogen bonded to said M;

CyC is selected from the group consisting of an unsubstituted $C_4$-$C_{60}$ carbocyclic group containing carbon bonded to said M, a substituted $C_4$-$C_{60}$ carbocyclic group containing carbon bonded to said M, an unsubstituted $C_3$-$C_{60}$ heterocyclic group containing carbon bonded to said M, a substituted $C_3$-$C_{60}$ heterocyclic group containing carbon bonded to said M, an unsubstituted $C_6$-$C_{60}$ aryl containing carbon bonded to said M, a substituted $C_6$-$C_{60}$ aryl containing carbon bonded to said M, an unsubstituted $C_3$-$C_{60}$ heteroaryl containing carbon bonded to said M, and a substituted $C_3$-$C_{60}$ heteroaryl containing carbon bonded to said M;

the CyN-CyC formed by said CyN and said CyC is a cyclometalating ligand bonded to said M through nitrogen (N) of said CyN and carbon (C) of said CyC;

each substituent of the CyN-CyC is independently selected from the group consisting of a halogen atom, —OR, —N(R)(R'), —P(R)(R'), —POR, —PO$_2$R, —PO$_3$R, —SR, —Si(R)(R')(R"), —B(R)(R'), —B(OR)(OR'), —C(O)R, —C(O)OR, —C(O)N(R), —CN, —NO$_2$, —SO$_2$, —SOR, —SO$_2$R, —SO$_3$R, substituted or unsubstituted $C_1$-$C_{20}$ alkyl, and substituted or unsubstituted $C_6$-$C_{20}$ aryl, the substituents are alternatively joined to form a substituted or unsubstituted 4- to 7-membered carbocyclic group or a substituted or unsubstituted 4- to 7-membered heterocyclic group, the R, R' and R" are independently selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

alternatively, the CyN-CyC is represented by the Formula 1a:

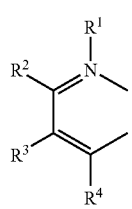

[Formula 1a]

wherein $R^1$, $R^2$, $R^3$, and $R^4$ are independently selected from the group consisting of hydrogen, halogen atom, —OR$^a$, —N(R$^a$)$_2$, —P(R$^a$)$_2$, —POR$^a$, —PO$_2$R$^a$, —PO$_3$R$^a$, —SR$^a$, —Si(R$^a$)$_3$, —B(R$^a$)$_2$, —B(OR$^a$)$_2$, —C(O)R$^a$, —C(O)OR$^a$, —C(O)N(R$^a$), —CN, —NO$_2$, —SO$_2$, —SOR$^a$, —SO$_2$R$^a$, —SO$_3$R$^a$, $C_1$-$C_{20}$ alkyl, and $C_6$-$C_{20}$ aryl, and R$^a$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

A is either an unsubstituted imidazole containing nitrogen bonded to said M, or one containing nitrogen bonded to said M selected from the group consisting of substituted or unsubstituted triethylamine, propylamine, cyclohexylamine, pyrrolidine, pyrroline, piperidine, indole, azaindole, carbazole, indazole, norharman, harman, aniline, oxazole, thiazole, pyrrole, benzimidazole, benzotriazole, benzoxazole, benzothiazole, benzoselenazole, benzothiadiazole, isoxazole, isothiazole, oxadiazole, thiadiazole, anthranyl, triazine, benzisoxazole, quinoline, benzoquinoline, acridine, thiazoline, quinuclidine, imidazoline, oxazoline, thiazoline, and isoquinoline;

X is a monoanionic monodentate ligand; and n is one of 1 and 2.

2. The organometallic complex of claim 1, wherein the CyN-CyC is represented by one of the following Formulas:

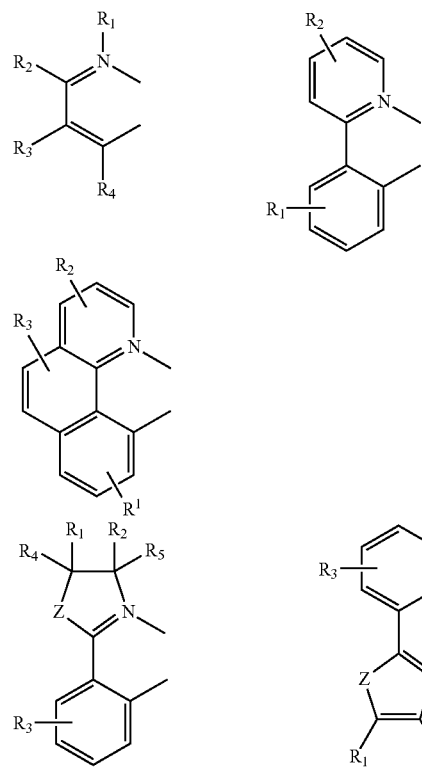

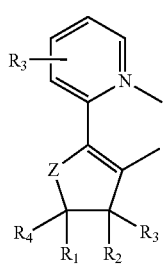
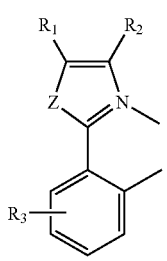
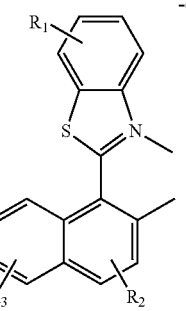
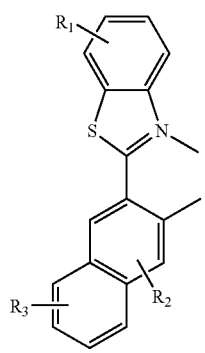
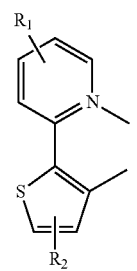
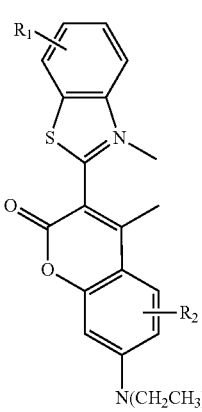
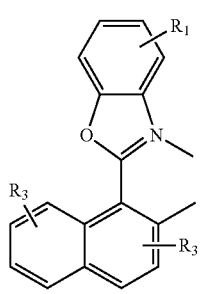
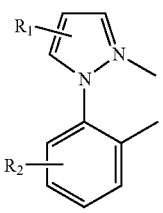
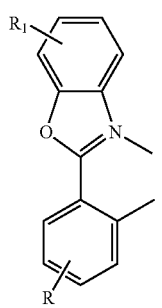
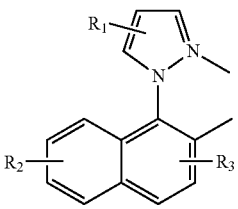
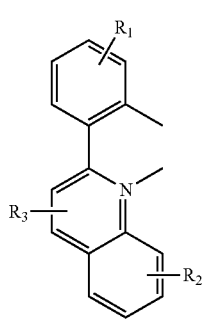
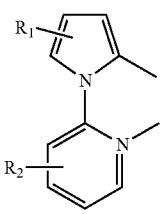

-continued

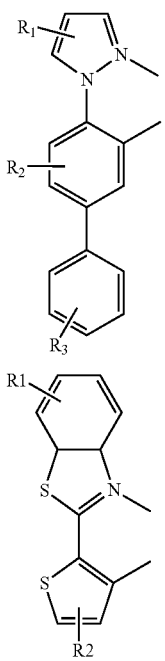
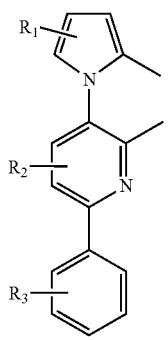
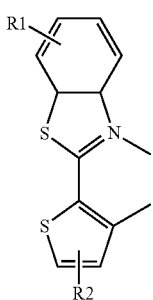

wherein $R_1$, $R_2$, $R_3$, $R_4$, and $R_5$ are independently selected from the group consisting of hydrogen, halogen atom, $-OR^b$, $-N(R^b)_2$, $-P(R^b)_2$, $-POR^b$, $-PO_2R^b$, $-PO_3R^b$, $-SR^b$, $-Si(R^b)_3$, $-B(R^b)_2$, $-B(OR^b)_2$, $-C(O)R^b$, $-C(O)OR^b$, $-C(O)N(R^b)$, $-CN$, $-NO_2$, $-SO_2$, $-SOR^b$, $-SO_2R^b$, $-SO_3R^b$, a $C_1$-$C_{20}$ alkyl, or a $C_6$-$C_{20}$ aryl group, and $R^b$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl; and Z is one of S, O, and $NR_0$ where $R_0$ is hydrogen or a $C_1$-$C_{20}$ alkyl group.

3. The organometallic complex of claim 1, wherein said X is selected from the group consisting of —F, —Cl, —Br, —I, —CN, —CN($R_{11}$), —SCN, and —OCN, and $R_{11}$ is a substituted or unsubstituted $C_1$-$C_{20}$ alkyl group.

4. The organometallic complex of claim 1, wherein said M is one of Ir and Pt.

5. An organometallic complex represented by one selected from the group consisting of compounds represented by Formulae 2, 3, and 5 through 14:

[Formula 2]

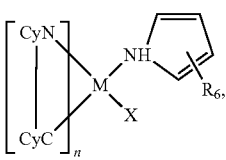

[Formula 3]

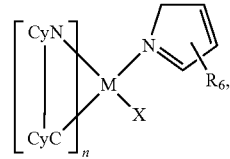

[Formula 5]

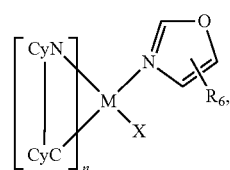

[Formula 6]

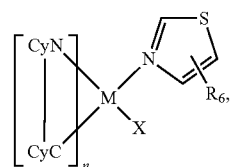

[Formula 7]

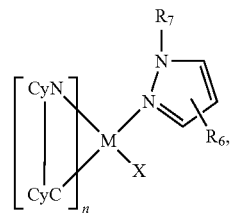

[Formula 8]

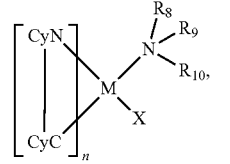

[Formula 9]

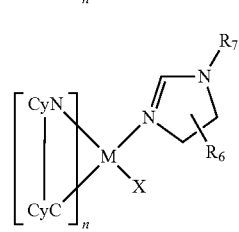

[Formula 10]

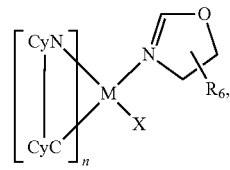

[Formula 11]

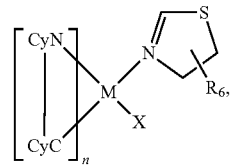

[Formula 12]

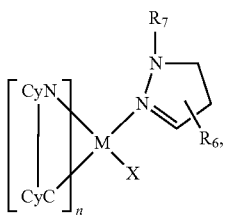

[Formula 13]

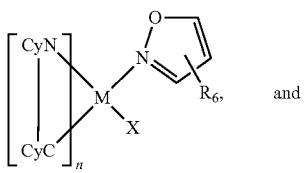 and

[Formula 14]

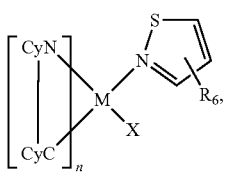

wherein M is a metal selected from the group consisting of Ir, Os, Pt, Pb, Re, Ru, and Pd;

CyN is selected from the group consisting of a substituted $C_3$-$C_{60}$ heterocyclic group containing nitrogen bonded to said M, an unsubstituted $C_3$-$C_{60}$ heterocyclic group containing nitrogen bonded to said M, a substituted $C_3$-$C_{60}$ heteroaryl group containing nitrogen bonded to said M, and an unsubstituted $C_3$-$C_{60}$ heteroaryl group containing nitrogen bonded to said M;

CyC is selected from the group consisting of an unsubstituted $C_4$-$C_{60}$ carbocyclic group containing carbon bonded to said M, a substituted $C_4$-$C_{60}$ carbocyclic group containing carbon bonded to said M, an unsubstituted $C_3$-$C_{60}$ heterocyclic group containing carbon bonded to said M, a substituted $C_3$-$C_{60}$ heterocyclic group containing carbon bonded to said M, an unsubstituted $C_6$-$C_{60}$ aryl containing carbon bonded to said M, a substituted $C_6$-$C_{60}$ aryl containing carbon bonded to said M, an unsubstituted $C_3$-$C_{60}$ heteroaryl containing carbon bonded to said M, and a substituted $C_3$-$C_{60}$ heteroaryl containing carbon bonded to said M;

the CyN-CyC formed by said CyN and said CyC is a cyclometalating ligand bonded to said M through nitrogen (N) of said CyN and carbon (C) of said CyC;

each substituent of the CyN-CyC is independently selected from the group consisting of a halogen atom, —OR, —N(R)(R'), —P(R)(R'), —POR, —PO$_2$R, —PO$_3$R, —SR, —Si(R)(R')(R"), —B(R)(R'), —B(OR)(OR'), —C(O)R, —C(O)OR, —C(O)N(R), —CN, —NO$_2$, —SO$_2$, —SOR, —SO$_2$R, —SO$_3$R, substituted or unsubstituted $C_1$-$C_{20}$ alkyl, and substituted or unsubstituted $C_6$-$C_{20}$ aryl, the substituents are alternatively joined to form a substituted or unsubstituted 4- to 7-membered carbocyclic group or a substituted or unsubstituted 4- to 7-membered heterocyclic group, the R, R' and R" are independently selected from the group consisting of hydrogen, a substituted or unsubstituted $C_1$-$C_{70}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

alternatively, the CyN-CyC is represented by the Formula 1a:

[Formula 1a]

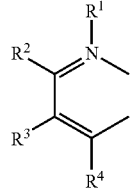

wherein $R^1$, $R^2$, $R^3$, and $R^4$ are independently selected from the group consisting of hydrogen, halogen atom, —OR$^a$, —N(R$^a$)$_2$, —P(R$^a$)$_2$, —POR$^a$, —PO$_2$R$^a$, —PO$_3$R$^a$, —SR$^a$, —Si(R$^a$)$_3$, —B(R$^a$)$_2$, —B(OR$^a$)$_2$, —C(O)R$^a$, —C(O)OR$^a$, —C(O)N(R$^a$), —CN, —NO$_2$—SO$_2$, —SOR$^a$, —SO$_2$R$^a$, —SO$_3$R$^a$, $C_1$-$C_{20}$ alkyl, and $C_6$-$C_{20}$ aryl, and R$^a$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

$R_6$ and $R_7$ are independently selected from the group consisting of hydrogen, halogen atom, —OR$^c$, —N(R$^c$)$_2$, —P(R$^c$)$_2$, —POR$^c$, —PO$_2$R$^c$, —PO$_3$R$^c$, SR$^c$, —Si(R$^c$)$_3$, —B(R$^c$)$_2$, —B(OR$^c$)$_2$, —C(O)R$^c$, —C(O)OR$^c$, —C(O)N(R$^c$), —CN, —NO$_2$, —SO$_2$, —SOW, —SO$_2$R$^c$, —SO$_3$R$^c$, substituted or unsubstituted $C_1$-$C_{20}$ alkyl, substituted or unsubstituted $C_6$-$C_{20}$ aryl or substituted or unsubstituted $C_2$-$C_{20}$ heteroaryl group, and R$^c$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

substituents of $R_6$ and $R_7$, which are substituted at different positions, are alternatively interconnected to form a substituted or unsubstituted fused 4-7 atom ring;

$R_8$, $R_9$, and $R_{10}$ are independently a substituted or unsubstituted $C_1$-$C_{20}$ alkyl, a substituted or unsubstituted $C_6$-$C_{20}$ aryl or substituted or unsubstituted $C_2$-$C_{20}$ heteroaryl group;

X is selected from the group consisting of F, Cl, Br, I, CN, CN(R$_{11}$), SCN or OCN, R$_{11}$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl; and n is one of 1 and 2.

6. An organic electroluminescent device, comprising:

a first electrode;

a second electrode; and an organic layer between said first electrode and said second electrode, said organic layer comprising an organometallic complex represented by Formula 1:

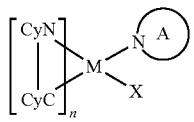

[Formula 1]

wherein M is a metal selected from the group consisting of Ir, Os, Pt, Pb, Re, Ru, and Pd;

CyN is selected from the group consisting of a substituted $C_3$-$C_{60}$ heterocyclic group containing nitrogen bonded to said M, an unsubstituted $C_3$-$C_{60}$ heterocyclic group containing nitrogen bonded to said M, a substituted $C_3$-$C_{60}$ heteroaryl group containing nitrogen bonded to said M, and an unsubstituted $C_3$-$C_{60}$ heteroaryl group containing nitrogen bonded to said M;

CyC is selected from the group consisting of an unsubstituted $C_4$-$C_{60}$ carbocyclic group containing carbon bonded to said M, a substituted $C_4$-$C_{60}$ carbocyclic group containing carbon bonded to said M, an unsubstituted $C_3$-$C_{60}$ heterocyclic group containing carbon bonded to said M, a substituted $C_3$-$C_{60}$ heterocyclic group containing carbon bonded to said M, an unsubstituted $C_6$-$C_{60}$ aryl containing carbon bonded to said M, a substituted $C_6$-$C_{60}$ aryl containing carbon bonded to said M, an unsubstituted $C_3$-$C_{60}$ heteroaryl containing carbon bonded to said M, and a substituted $C_3$-$C_{60}$ heteroaryl containing carbon bonded to said M;

the CyN-CyC formed by said CyN and said CyC is a cyclometalating ligand bonded to said M through nitrogen (N) of said CyN and carbon (C) of said CyC;

each substituent of the CyN-CyC is independently selected from the group consisting of a halogen atom, —OR, —N(R)(R'), —P(R)(R'), —POR, —$PO_2R$, —$PO_3R$, —SR, —Si(R)(R')(R''), —B(R)(R'), —B(OR)(OR'), —C(O)R, —C(O)OR, —C(O)N(R), —CN, —$NO_2$, —$SO_2$, —SOR, —$SO_2R$, —$SO_3R$, substituted or unsubstituted $C_1$-$C_{20}$ alkyl, and substituted or unsubstituted $C_6$-$C_{20}$ aryl, the substituents are alternatively joined to form a substituted or unsubstituted 4- to 7-membered carbocyclic group or a substituted or unsubstituted 4- to 7-membered heterocyclic group, the R, R' and R'' are independently selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

alternatively, the CyN-CyC is represented by the Formula 1a:

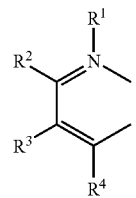

[Formula 1a]

wherein $R^1$, $R^2$, $R^3$, and $R^4$ are independently selected from the group consisting of hydrogen, halogen atom, —$OR^a$, —$N(R^a)_2$, —$P(R^a)_2$, —$POR^a$, —$PO_2R^a$, —$PO_3R^a$, —$SR^a$, —$Si(R^a)_3$, —$B(R^a)_2$, —$B(OR^a)_2$, —$C(O)R^a$, —$C(O)OR^a$, —$C(O)N(R^a)$, —CN, —$NO_2$, —$SO_2$, —$SOR^a$, —$SO_2R^a$, —$SO_3R^a$, $C_1$-$C_{20}$ alkyl, and $C_6$-$C_{20}$ aryl, and $R^a$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

A is either imidazole containing nitrogen bonded to said M, or one containing nitrogen bonded to said M selected from the group consisting of substituted or unsubstituted triethylamine, propylamine, cyclohexylamine, pyrrolidine, pyrroline, piperidine, indole, azaindole, carbazole, indazole, norharman, harman, aniline, oxazole, thiazole, pyrrole, benzimidazole, benzotriazole, benzoxazole, benzothiazole, benzoselenazole, benzothiadiazole, isoxazole, isothiazole, oxadiazole, thiadiazole, anthranyl, triazine, benzisoxazole, quinoline, benzoquinoline, acridine, thiazoline, quinuclidine, imidazoline, oxazoline, thiazoline, and isoquinoline;

X is a monoanionic monodentate ligand; and n is one of 1 and 2.

7. The organic electroluminescent device of claim 6, wherein the CyN-CyC is represented by one of the following Formulas:

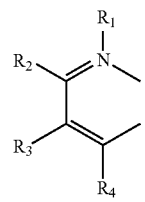 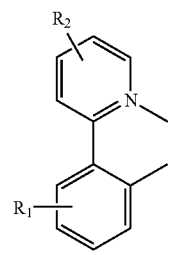

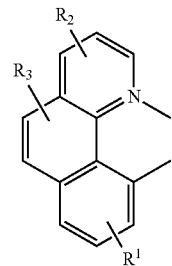

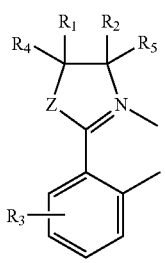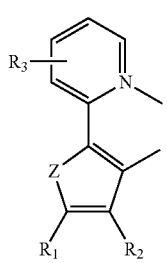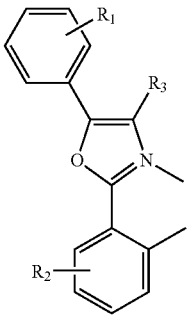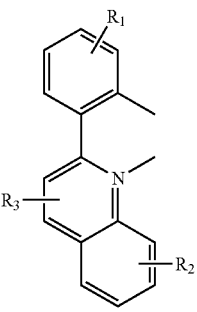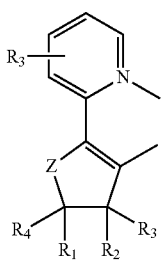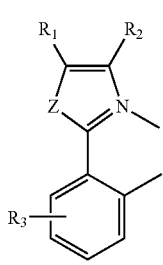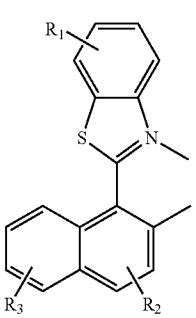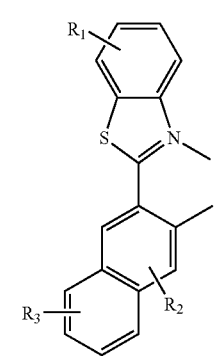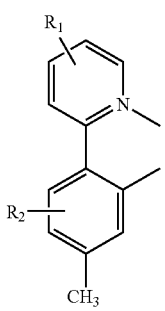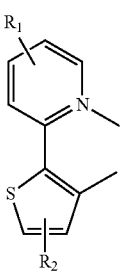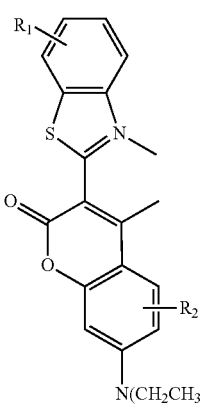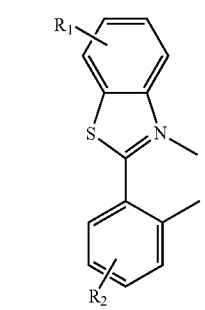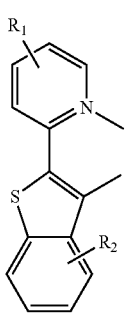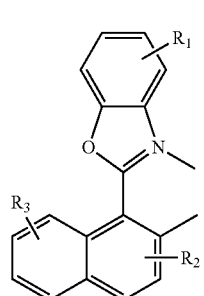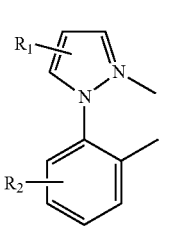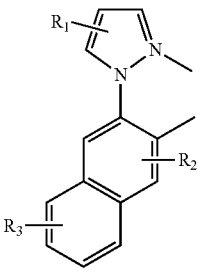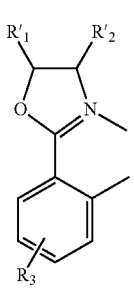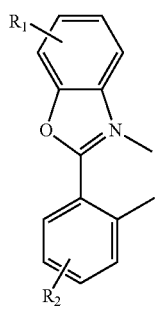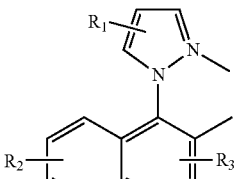

-continued

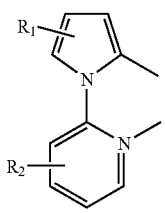
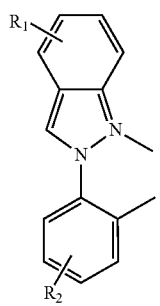
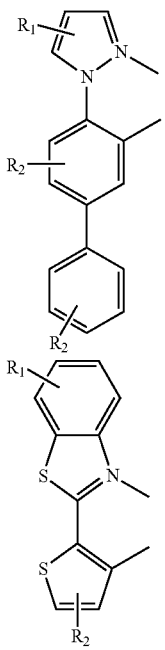
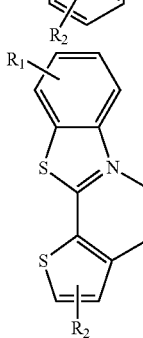
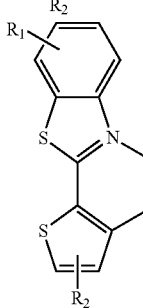

wherein $R_1$, $R_2$, $R_3$, $R_4$, and $R_5$ are independently selected from the group consisting of hydrogen, halogen atom, —$OR^b$, —$N(R^b)_2$, —$P(R^b)_2$, —$POR^b$, —$PO_2R^b$, —$PO_3R^b$, —$SR^b$, —$Si(R^b)_3$, —$B(R^b)_2$, —$B(OR^b)_2$, —$C(O)R^b$, —$C(O)OR^b$, —$C(O)N(R^b)$, —CN, —$NO_2$, —$SO_2$, —$SOR^b$, —$SO_2R^b$, —$SO_3R^b$, a $C_1$-$C_{20}$ alkyl, or a $C_6$-$C_{20}$ aryl group, and $R^b$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl; and Z is one of S, O, and $NR_0$ where $R_0$ is hydrogen or a $C_1$-$C_{20}$ alkyl group.

8. The organic electroluminescent device of claim 6, wherein said X is selected from the group consisting of —F, —Cl, —Br, —I, —CN, —$CN(R_{11})$, —SCN, and —OCN, and $R_{11}$ is a substituted or unsubstituted $C_1$-$C_{20}$ alkyl group.

9. The organic electroluminescent device of claim 6, wherein said M is one of Ir and Pt.

10. An organic electroluminescent device comprising:
a first electrode;
a second electrode; and
an organic layer between said first electrode and said second electrode, said organic layer comprising an organo-metallic complex represented by one selected from the group consisting of compounds represented by Formulae 2 through 14:

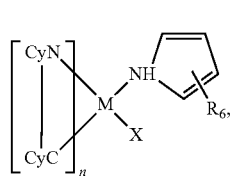
[Formula 2]

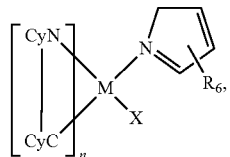
[Formula 3]

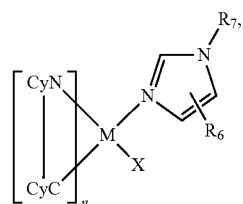
[Formula 4]

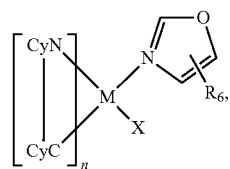
[Formula 5]

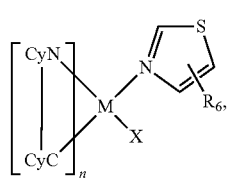
[Formula 6]

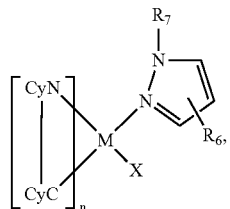
[Formula 7]

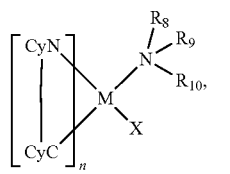
[Formula 8]

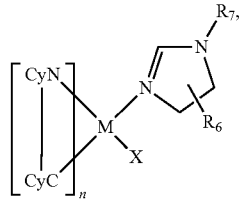
[Formula 9]

-continued

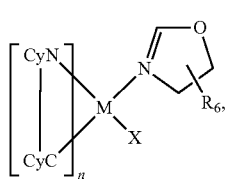

[Formula 10]

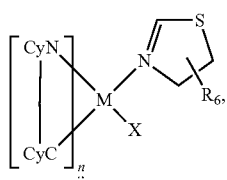

[Formula 11]

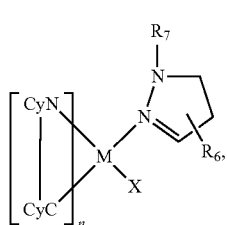

[Formula 12]

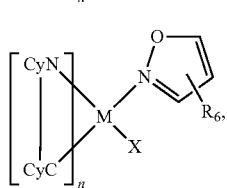

[Formula 13]

and

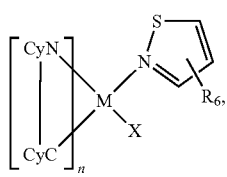

[Formula 14]

wherein M is a metal selected from the group consisting of Ir, Os, Pt, Pb, Re, Ru, and Pd;

CyN is selected from the group consisting of a substituted $C_3$-$C_{60}$ heterocyclic group containing nitrogen bonded to said M, an unsubstituted $C_3$-$C_{60}$ heterocyclic group containing nitrogen bonded to said M, a substituted $C_3$-$C_{60}$ heteroaryl group containing nitrogen bonded to said M, and an unsubstituted $C_3$-$C_{60}$ heteroaryl group containing nitrogen bonded to said M;

CyC is selected from the group consisting of an unsubstituted $C_4$-$C_{60}$ carbocyclic group containing carbon bonded to said M, a substituted $C_4$-$C_{60}$ carbocyclic group containing carbon bonded to said M, an unsubstituted $C_3$-$C_{60}$ heterocyclic group containing carbon bonded to said M, a substituted $C_3$-$C_{60}$ heterocyclic group containing carbon bonded to said M, an unsubstituted $C_6$-$C_{60}$ aryl containing carbon bonded to said M, a substituted $C_6$-$C_{60}$ aryl containing carbon bonded to said M, an unsubstituted $C_3$-$C_{60}$ heteroaryl containing carbon bonded to said M, and a substituted $C_3$-$C_{60}$ heteroaryl containing carbon bonded to said M;

the CyN-CyC formed by said CyN and said CyC is a cyclometalating ligand bonded to said M through nitrogen (N) of said CyN and carbon (C) of said CyC;

each substituent of the CyN-CyC is independently selected from the group consisting of a halogen atom, —OR, —N(R)(R'), —P(R)(R'), —POR, —PO$_2$R, —PO$_3$R, —SR, —Si(R)(R')(R"), —B(R)(R'), —B(OR)(OR'), —C(O)R, —C(O)OR, —C(O)N(R), —CN, —NO$_2$, —SO$_2$, —SOR, —SO$_2$R, —SO$_3$R, substituted or unsubstituted $C_1$-$C_{20}$ alkyl, and substituted or unsubstituted $C_6$-$C_{20}$ aryl, the substituents are alternatively joined to form a substituted or unsubstituted 4- to 7-membered carbocyclic group or a substituted or unsubstituted 4- to 7-membered heterocyclic group, the R, R' and R" are independently selected from the group consisting of hydrogen, a substituted or unsubstituted $C_1$-$C_{70}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

alternatively, the CyN-CyC is represented by the Formula 1a:

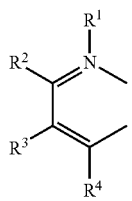

[Formula 1a]

wherein $R^1$, $R^2$, $R^3$, and $R^4$ are independently selected from the group consisting of hydrogen, halogen atom, —OR$^a$, —N(R$^a$)$_2$, —P(R$^a$)$_2$, —POR$^a$, —PO$_2$R$^a$— PO$_3$R$^a$, —SR$^a$, —Si(R$^a$)$_3$, —B(R$^a$)$_2$—, —B(OR$^a$)$_2$, —C(O)R$^a$, —C(O)OR$^a$, —C(O)N(R$^a$), —CN, —NO$_2$—SO$_2$, —SOR$^a$, —SO$_2$R$^a$—SO$_3$R$^a$, $C_1$-$C_{20}$ alkyl, and $C_6$-$C_{20}$ aryl, and $R^a$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

$R_6$ and $R_7$ are independently selected from the group consisting of hydrogen, halogen atom, —OR$^c$, —N(R$^c$)$_2$, —P(R$^c$)$_2$, —POR$^c$, —PO$_2$R$^c$, —PO$_3$R$^c$, —SR$^c$, —Si (R$^c$)$_3$, —B(R$^c$)$_2$, —B(OR$^c$)$_2$, —C(O)R$^c$, —C(O)OR$^c$, —C(O)N(R$^c$), —CN, —NO$_2$, —SO$_2$, —SOW, —SO$_2$R$^c$, —SO$_3$R$^c$, substituted or unsubstituted $C_1$-$C_{20}$ alkyl, substituted or unsubstituted $C_6$-$C_{20}$ aryl or substituted or unsubstituted $C_2$-$C_{20}$ heteroaryl group, and R$^c$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

substituents of $R_6$ and $R_7$, which are substituted at different positions, are alternatively interconnected to form a substituted or unsubstituted fused 4-7 atom ring;

$R_8$, $R_9$, and $R_{10}$ are independently a substituted or unsubstituted $C_1$-$C_{20}$ alkyl, a substituted or unsubstituted $C_6$-$C_{20}$ aryl or substituted or unsubstituted $C_2$-$C_{20}$ heteroaryl group;

X is selected from the group consisting of F, Cl, Br, I, CN, CN($R_{11}$), SCN or OCN, $R_{11}$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl; and n is one of 1 and 2.

11. The organic electroluminescent device of claim 6, wherein the organometallic complex represented by Formula 1 is doped to at least one selected from the group consisting of a polymer host, a mixture of a polymer host and a small molecular host, a small molecular host, and non-luminous polymer matrix.

12. An organometallic complex represented by Formula 4:

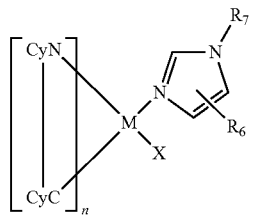

[Formula 4]

wherein M is a metal selected from the group consisting of Ir, Os, Pt, Pb, Re, Ru, and Pd;

CyN is selected from the group consisting of a substituted $C_3$-$C_{60}$ heterocyclic group containing nitrogen bonded to said M, an unsubstituted $C_3$-$C_{60}$ heterocyclic group containing nitrogen bonded to said M, a substituted $C_3$-$C_{60}$ heteroaryl group containing nitrogen bonded to said M, and an unsubstituted $C_3$-$C_{60}$ heteroaryl group containing nitrogen bonded to said M;

CyC is selected from the group consisting of an unsubstituted $C_4$-$C_{60}$ carbocyclic group containing carbon bonded to said M, a substituted $C_4$-$C_{60}$ carbocyclic group containing carbon bonded to said M, an unsubstituted $C_3$-$C_{60}$ heterocyclic group containing carbon bonded to said M, a substituted $C_3$-$C_{60}$ heterocyclic group containing carbon bonded to said M, an unsubstituted $C_6$-$C_{60}$ aryl containing carbon bonded to said M, a substituted $C_6$-$C_{60}$ aryl containing carbon bonded to said M, an unsubstituted $C_3$-$C_{60}$ heteroaryl containing carbon bonded to said M, and a substituted $C_3$-$C_{60}$ heteroaryl containing carbon bonded to said M;

the CyN-CyC formed by said CyN and said CyC is a cyclometalating ligand bonded to said M through nitrogen (N) of said CyN and carbon (C) of said CyC;

each substituent of the CyN-CyC is independently selected from the group consisting of a halogen atom, —OR, —N(R)(R'), —P(R)(R'), —POR, —PO₂R, —PO₃R, —SR, —Si(R)(R')(R"), —B(R)(R'), —B(OR)(OR'), —C(O)R, —C(O)OR, —C(O)N(R), —CN, —NO₂, —SO₂, —SOR, —SO₂R, —SO₃R, substituted or unsubstituted $C_1$-$C_{20}$ alkyl, and substituted or unsubstituted $C_6$-$C_{20}$ aryl, the substituents are alternatively joined to form a substituted or unsubstituted 4- to 7-membered carbocyclic group or a substituted or unsubstituted 4- to 7-membered heterocyclic group, the R, R' and R" are independently selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

alternatively, the CyN-CyC is represented by the Formula 1a:

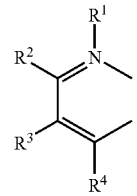

[Formula 1a]

wherein $R^1$, $R^2$, $R^3$, and $R^4$ are independently selected from the group consisting of hydrogen, halogen atom, —OR$^a$, —N(R$^a$)₂, —P(R$^a$)₂, —POR$^a$, —PO₂R$^a$, —PO₃R$^a$, —SR$^a$, —Si(R$^a$)₃, —B(R$^a$)₂, —B(OR$^a$)₂, —C(O)R$^a$, —C(O)ORa, —C(O)N(R$^a$), —CN, —NO₂, —SO₂, —SOR$^a$, —SO₂R$^a$, —SO₃R$^a$, $C_1$-$C_{20}$ alkyl, and $C_6$-$C_{20}$ aryl, and R$^a$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

$R_6$ is selected from the group consisting of hydrogen, halogen atom, —OR$^c$, —N(R$^c$)₂, —P(R$^c$)₂, —POR$^c$, —PO₂R$^c$, —PO₃R$^c$, —SR$^c$, —Si(R$^c$)₃, —B(R$^c$)₂, —B(OR$^c$)₂, —C(O)R$^c$, —C(O)OR$^c$, —C(O)N(R$^c$), —CN, —NO₂, —SO₂, —SOR$^c$, —SO₂R$^c$, —SO₃R$^c$, substituted or unsubstituted $C_1$-$C_{20}$ alkyl, substituted or unsubstituted $C_6$-$C_{20}$ aryl or substituted or unsubstituted $C_2$-$C_{20}$ heteroaryl group, and R$^c$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

$R_7$ is selected from the group consisting of hydrogen, halogen atom, —OR$^c$, —N(R$^c$)₂, —P(R$^c$)₂, —POR$^c$, —PO₂R$^c$, —PO₃R$^c$, —SR$^c$, —Si(R$^c$)₃, —B(R$^c$)₂, —B(OR$^c$)$_2$, —C(O)R$^c$, —C(O)OR$^c$, —C(O)N(R$^c$), —CN, —NO$_2$, —SO$_2$, —SOW, —SO$_2$R$^c$, —SO$_3$R$^c$, substituted or unsubstituted C$_2$-C$_{20}$ alkyl, substituted or unsubstituted C$_6$-C$_{20}$ aryl or substituted or unsubstituted C$_2$-C$_{20}$ heteroaryl group, and R$^c$ is selected from the group consisting of hydrogen, a substituted or unsubstituted C$_1$-C$_{20}$ alkyl, substituted or unsubstituted C$_1$-C$_{20}$ alkoxy, substituted or unsubstituted C$_2$-C$_{20}$ alkenyl, substituted or unsubstituted C$_2$-C$_{20}$ alkynyl, substituted or unsubstituted C$_1$-C$_{20}$ heteroalkyl, substituted or unsubstituted C$_6$-C$_{40}$ aryl, substituted or unsubstituted C$_7$-C$_{40}$ arylalkyl, substituted or unsubstituted C$_7$-C$_{40}$ alkylaryl, substituted or unsubstituted C$_2$-C$_{40}$ heteroaryl, and substituted or unsubstituted C$_3$-C$_{40}$ heteroarylalkyl;

substituents of R$_6$ and R$_7$, which are substituted at different positions, are alternatively interconnected to form a substituted or unsubstituted fused 4-7 atom ring; and R$_6$ and R$_7$ are not hydrogen at the same time;

X is selected from the group consisting of F, Br, I, CN, CN(R$_{11}$), SCN or OCN, R$_{11}$ is selected from the group consisting of hydrogen, a substituted or unsubstituted C$_1$-C$_{20}$ alkyl, substituted or unsubstituted C$_1$-C$_{20}$ alkoxy, substituted or unsubstituted C$_2$-C$_{20}$ alkenyl, substituted or unsubstituted C$_2$-C$_{20}$ alkynyl, substituted or unsubstituted C$_1$-C$_{20}$ heteroalkyl, substituted or unsubstituted C$_6$-C$_{40}$ aryl, substituted or unsubstituted C$_7$-C$_{40}$ arylalkyl, substituted or unsubstituted C$_7$-C$_{40}$ alkylaryl, substituted or unsubstituted C$_2$-C$_{40}$ heteroaryl, and substituted or unsubstituted C$_3$-C$_{40}$ heteroarylalkyl; and n is one of 1 and 2.

13. An organometallic complex represented by Formula 1:

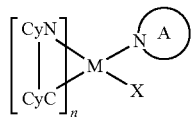

[Formula 1]

wherein M is a metal selected from the group consisting of Ir, Os, Pt, Pb, Re, Ru, and Pd;

CyN is selected from the group consisting of a substituted C$_3$-C$_{60}$ heterocyclic group containing nitrogen bonded to said M, an unsubstituted C$_3$-C$_{60}$ heterocyclic group containing nitrogen bonded to said M, a substituted C$_3$-C$_{60}$ heteroaryl group containing nitrogen bonded to said M, and an unsubstituted C$_3$-C$_{60}$ heteroaryl group containing nitrogen bonded to said M;

CyC is selected from the group consisting of an unsubstituted C$_4$-C$_{60}$ carbocyclic group containing carbon bonded to said M, a substituted C$_4$-C$_{60}$ carbocyclic group containing carbon bonded to said M, an unsubstituted C$_3$-C$_{60}$ heterocyclic group containing carbon bonded to said M, a substituted C$_3$-C$_{60}$ heterocyclic group containing carbon bonded to said M, an unsubstituted C$_6$-C$_{60}$ aryl containing carbon bonded to said M, a substituted C$_6$-C$_{60}$ aryl containing carbon bonded to said M, an unsubstituted C$_3$-C$_{60}$ heteroaryl containing carbon bonded to said M, and a substituted C$_3$-C$_{60}$ heteroaryl containing carbon bonded to said M;

the CyN-CyC formed by said CyN and said CyC is a cyclometalating ligand bonded to said M through nitrogen (N) of said CyN and carbon (C) of said CyC;

each substituent of the CyN-CyC is independently selected from the group consisting of a halogen atom, —OR, —N(R)(R'), —P(R)(R'), —POR, —PO$_2$R, —PO$_3$R, —SR, —Si(R)(R')(R''), —B(R)(R'), —B(OR)(OR'), —C(O)R, —C(O)OR, —C(O)N(R), —CN, —NO$_2$, —SO$_2$, —SOR, —SO$_2$R, —SO$_3$R, substituted or unsubstituted C$_1$-C$_{20}$ alkyl, and substituted or unsubstituted C$_6$-C$_{20}$ aryl, the substituents are alternatively joined to form a substituted or unsubstituted 4- to 7-membered carbocyclic group or a substituted or unsubstituted 4- to 7-membered heterocyclic group, the R, R' and R'' are independently selected from the group consisting of hydrogen, a substituted or unsubstituted C$_1$-C$_{20}$ alkyl, substituted or unsubstituted C$_1$-C$_{20}$ alkoxy, substituted or unsubstituted C$_2$-C$_{20}$ alkenyl, substituted or unsubstituted C$_2$-C$_{20}$ alkynyl, substituted or unsubstituted C$_1$-C$_{20}$ heteroalkyl, substituted or unsubstituted C$_6$-C$_{40}$ aryl, substituted or unsubstituted C$_7$-C$_{40}$ arylalkyl, substituted or unsubstituted C$_7$-C$_{40}$ alkylaryl, substituted or unsubstituted C$_2$-C$_{40}$ heteroaryl, and substituted or unsubstituted C$_3$-C$_{40}$ heteroarylalkyl;

alternatively, the CyN-CyC is represented by the Formula 1a:

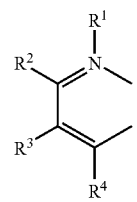

[Formula 1a]

wherein R$^1$, R$^2$, R$^3$, and R$^4$ are independently selected from the group consisting of hydrogen, halogen atom, —OR$^a$, —N(R$^a$)$_2$, —P(R$^a$)$_2$, —POR$^a$, —PO$_2$R$^a$, —PO$_3$R$^a$, —SR$^a$, —Si(R$^a$)$_3$, —B(R$^a$)$_2$, —B(OR$^a$)$_2$, —C(O)R$^a$, —C(O)OR$^a$, —C(O)N(R$^a$), —CN, —NO$_2$, —SO$_2$, —SOR$^a$, —SO$_2$R$^a$, —SO$_3$R$^a$, C$_1$-C$_{20}$ alkyl, and C$_6$-C$_{20}$ aryl, and R$^a$ is selected from the group consisting of hydrogen, a substituted or unsubstituted C$_1$-C$_{20}$ alkyl, substituted or unsubstituted C$_1$-C$_{20}$ alkoxy, substituted or unsubstituted C$_2$-C$_{20}$ alkenyl, substituted or unsubstituted C$_2$-C$_{20}$ alkynyl, substituted or unsubstituted C$_1$-C$_{20}$ heteroalkyl, substituted or unsubstituted C$_6$-C$_{40}$ aryl, substituted or unsubstituted C$_7$-C$_{40}$ arylalkyl, substituted or unsubstituted C$_7$-C$_{40}$ alkylaryl, substituted or unsubstituted C$_2$-C$_{40}$ heteroaryl, and substituted or unsubstituted C$_3$-C$_{40}$ heteroarylalkyl;

A is one containing nitrogen bonded to said M selected from the group consisting of unsubstituted pyrimidine, unsubstituted pyrazole, and unsubstituted pyrazine;

X is —OCN; and n is one of 1 and 2.

14. An organic electroluminescent device, comprising:

a first electrode;

a second electrode; and an organic layer between said first electrode and said second electrode, said organic layer comprising an organometallic complex represented by Formula 1:

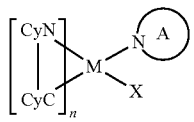

[Formula 1]

wherein M is a metal selected from the group consisting of Ir, Os, Pt, Pb, Re, Ru, and Pd;

CyN is selected from the group consisting of a substituted $C_3$-$C_{60}$ heterocyclic group containing nitrogen bonded to said M, an unsubstituted $C_3$-$C_{60}$ heterocyclic group containing nitrogen bonded to said M, a substituted $C_3$-$C_{60}$ heteroaryl group containing nitrogen bonded to said M, and an unsubstituted $C_3$-$C_{60}$ heteroaryl group containing nitrogen bonded to said M;

CyC is selected from the group consisting of an unsubstituted $C_4$-$C_{60}$ carbocyclic group containing carbon bonded to said M, a substituted $C_4$-$C_{60}$ carbocyclic group containing carbon bonded to said M, an unsubstituted $C_3$-$C_{60}$ heterocyclic group containing carbon bonded to said M, a substituted $C_3$-$C_{60}$ heterocyclic group containing carbon bonded to said M, an unsubstituted $C_6$-$C_{60}$ aryl containing carbon bonded to said M, a substituted $C_6$-$C_{60}$ aryl containing carbon bonded to said M, an unsubstituted $C_3$-$C_{60}$ heteroaryl containing carbon bonded to said M, and a substituted $C_3$-$C_{60}$ heteroaryl containing carbon bonded to said M;

the CyN-CyC formed by said CyN and said CyC is a cyclometalating ligand bonded to said M through nitrogen (N) of said CyN and carbon (C) of said CyC;

each substituent of the CyN-CyC is independently selected from the group consisting of a halogen atom, —OR, —N(R)(R'), —P(R)(R'), —POR, —$PO_2R$, —$PO_3R$, —SR, —Si(R)(R')(R''), —B(R)(R'), —B(OR)(OR'), —C(O)R, —C(O)OR, —C(O)N(R), —CN, —$NO_2$, —$SO_2$, —SOR, —$SO_2R$, —$SO_3R$, substituted or unsubstituted $C_1$-$C_{20}$ alkyl, and substituted or unsubstituted $C_6$-$C_{20}$ aryl, the substituents are alternatively joined to form a substituted or unsubstituted 4- to 7-membered carbocyclic group or a substituted or unsubstituted 4- to 7-membered heterocyclic group, the R, R' and R'' are independently selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

alternatively, the CyN-CyC is represented by the Formula 1a:

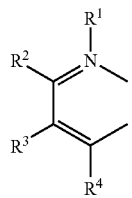

[Formula 1a]

wherein $R^1$, $R^2$, $R^3$, and $R^4$ are independently selected from the group consisting of hydrogen, halogen atom, —$OR^a$, —$N(R^a)_2$, —$P(R^a)_2$, —$POR^a$, —$PO_2R^a$, —$PO_3R^a$, —$SR^a$, —$Si(R^a)_3$, —$B(R^a)_2$, —$B(OR^a)_2$, —$C(O)R^a$, —$C(O)OR^a$, —$C(O)N(R^a)$, —CN, —$NO_2$, —$SO_2$, —$SOR^a$, —$SO_2R^a$, —$SO_3R^a$, $C_1$-$C_{20}$ alkyl, and $C_6$-$C_{20}$ aryl, and $R^a$ is selected from the group consisting of hydrogen, a substituted or unsubstituted $C_1$-$C_{20}$ alkyl, substituted or unsubstituted $C_1$-$C_{20}$ alkoxy, substituted or unsubstituted $C_2$-$C_{20}$ alkenyl, substituted or unsubstituted $C_2$-$C_{20}$ alkynyl, substituted or unsubstituted $C_1$-$C_{20}$ heteroalkyl, substituted or unsubstituted $C_6$-$C_{40}$ aryl, substituted or unsubstituted $C_7$-$C_{40}$ arylalkyl, substituted or unsubstituted $C_7$-$C_{40}$ alkylaryl, substituted or unsubstituted $C_2$-$C_{40}$ heteroaryl, and substituted or unsubstituted $C_3$-$C_{40}$ heteroarylalkyl;

A is one containing nitrogen bonded to said M selected from the group consisting of unsubstituted pyrimidine, unsubstituted pyrazole, and unsubstituted pyrazine;

X is —OCN; and n is one of 1 and 2.

15. An organic electroluminescent device, comprising:

a first electrode;

a second electrode; and an organic layer between said first electrode and said second electrode, said organic layer comprising an organometallic complex represented by Formula 4:

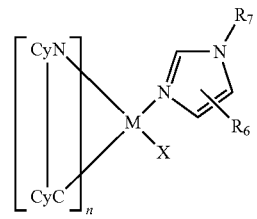

[Formula 4]

wherein M is a metal selected from the group consisting of Ir, Os, Pt, Pb, Re, Ru, and Pd;

CyN is selected from the group consisting of a substituted $C_3$-$C_{60}$ heterocyclic group containing nitrogen bonded to said M, an unsubstituted $C_3$-$C_{60}$ heterocyclic group containing nitrogen bonded to said M, a substituted $C_3$-$C_{60}$ heteroaryl group containing nitrogen bonded to said M, and an unsubstituted $C_3$-$C_{60}$ heteroaryl group containing nitrogen bonded to said M;

CyC is selected from the group consisting of an unsubstituted $C_4$-$C_{60}$ carbocyclic group containing carbon bonded to said M, a substituted $C_4$-$C_{60}$ carbocyclic group containing carbon bonded to said M, an unsubstituted $C_3$-$C_{60}$ heterocyclic group containing carbon bonded to said M, a substituted $C_3$-$C_{60}$ heterocyclic group containing carbon bonded to said M, an unsubstituted $C_6$-$C_{60}$ aryl containing carbon bonded to said M, a substituted $C_6$-$C_{60}$ aryl containing carbon bonded to said M, an unsubstituted $C_3$-$C_{60}$ heteroaryl containing carbon bonded to said M, and a substituted $C_3$-$C_{60}$ heteroaryl containing carbon bonded to said M;

the CyN-CyC formed by said CyN and said CyC is a cyclometalating ligand bonded to said M through nitrogen (N) of said CyN and carbon (C) of said CyC;

each substituent of the CyN-CyC is independently selected from the group consisting of a halogen atom, —OR, —N(R)(R'), —P(R)(R'), —POR, —$PO_2R$, —$PO_3R$, —SR, —Si(R)(R')(R"), —B(R)(R'), —B(OR)(OR'), —C(O)R, —C(O)OR, —C(O)N(R), —CN, —NO$_2$, —SO$_2$, —SOR, —SO$_2$R, —SO$_3$R, substituted or unsubstituted C$_1$-C$_{20}$ alkyl, and substituted or unsubstituted C$_6$-C$_{20}$ aryl, the substituents are alternatively joined to form a substituted or unsubstituted 4- to 7-membered carbocyclic group or a substituted or unsubstituted 4- to 7-membered heterocyclic group, the R, R' and R" are independently selected from the group consisting of hydrogen, a substituted or unsubstituted C$_1$-C$_{20}$ alkyl, substituted or unsubstituted C$_1$-C$_{20}$ alkoxy, substituted or unsubstituted C$_2$-C$_{20}$ alkenyl, substituted or unsubstituted C$_2$-C$_{20}$ alkynyl, substituted or unsubstituted C$_1$-C$_{20}$ heteroalkyl, substituted or unsubstituted C$_6$-C$_{40}$ aryl, substituted or unsubstituted C$_7$-C$_{40}$ arylalkyl, substituted or unsubstituted C$_7$-C$_{40}$ alkylaryl, substituted or unsubstituted C$_2$-C$_{40}$ heteroaryl, and substituted or unsubstituted C$_3$-C$_{40}$ heteroarylalkyl;

alternatively, the CyN-CyC is represented by the Formula 1a:

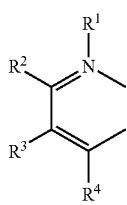

[Formula 1a]

wherein R$^1$, R$^2$, R$^3$, and R$^4$ are independently selected from the group consisting of hydrogen, halogen atom, —OR$^a$, —N(R$^a$)$_2$, —P(R$^a$)$_2$, —POR$^a$, —PO$_2$R$^a$, —PO$_3$R$^a$, —SR$^a$, —Si(R$^a$)$_3$, —B(R$^a$)$_2$, —B(OR$^a$)$_2$, —C(O)R$^a$, —C(O)OR$^a$, —C(O)N(R$^a$), —CN, —NO$_2$, —SO$_2$, —SOR$^a$, —SO$_2$R$^a$, —SO$_3$R$^a$, C$_1$-C$_{20}$ alkyl, and C$_6$-C$_{20}$ aryl, and R$^a$ is selected from the group consisting of hydrogen, a substituted or unsubstituted C$_1$-C$_{20}$ alkyl, substituted or unsubstituted C$_1$-C$_{20}$ alkoxy, substituted or unsubstituted C$_2$-C$_{20}$ alkenyl, substituted or unsubstituted C$_2$-C$_{20}$ alkynyl, substituted or unsubstituted C$_1$-C$_{20}$ heteroalkyl, substituted or unsubstituted C$_6$-C$_{40}$ aryl, substituted or unsubstituted C$_7$-C$_{40}$ arylalkyl, substituted or unsubstituted C$_7$-C$_{40}$ alkylaryl, substituted or unsubstituted C$_2$-C$_{40}$ heteroaryl, and substituted or unsubstituted C$_3$-C$_{40}$ heteroarylalkyl;

R$_6$ is selected from the group consisting of hydrogen, halogen atom, —OR$^c$, —N(R$^c$)$_2$, —P(R$^c$)$_2$, —POR$^c$, —PO$_2$R$^c$, —PO$_3$R$^c$, —SR$^c$, —Si(R$^c$)$_3$, —B(R$^c$)$_2$, —B(OR$^c$)$_2$, —C(O)R$^c$, —C(O)OR$^c$, —C(O)N(R$^c$), —CN, —NO$_2$, —SO$_2$, —SOR$^c$, —SO$_2$R$^c$, —SO$_3$R$^c$, substituted or unsubstituted C$_1$-C$_{20}$ alkyl, substituted or unsubstituted C$_6$-C$_{20}$ aryl or substituted or unsubstituted C$_2$-C$_{20}$ heteroaryl group, and R$^c$ is selected from the group consisting of hydrogen, a substituted or unsubstituted C$_1$-C$_{20}$ alkyl, substituted or unsubstituted C$_1$-C$_{20}$ alkoxy, substituted or unsubstituted C$_2$-C$_{20}$ alkenyl, substituted or unsubstituted C$_2$-C$_{20}$ alkynyl, substituted or unsubstituted C$_1$-C$_{20}$ heteroalkyl, substituted or unsubstituted C$_6$-C$_{40}$ aryl, substituted or unsubstituted C$_7$-C$_{40}$ arylalkyl, substituted or unsubstituted C$_7$-C$_{40}$ alkylaryl, substituted or unsubstituted C$_2$-C$_{40}$ heteroaryl, and substituted or unsubstituted C$_3$-C$_{40}$ heteroarylalkyl;

R$_7$ is selected from the group consisting of hydrogen, halogen atom, —OR$^c$, —N(R$^c$)$_2$, —P(R$^c$)$_2$, —POR$^c$, —PO$_2$R$^c$, —PO$_3$R$^c$, —SR$^c$, —Si(R$^c$)$_3$, —B(R$^c$)$_2$, —B(OR$^c$)$_2$, —C(O)R$^c$, —C(O)OR$^c$, —C(O)N(R$^c$), —CN, —NO$_2$, —SO$_2$, —SOR$^c$, —SO$_2$R$^c$, —SO$_3$R$^c$, substituted or unsubstituted C$_2$-C$_{20}$ alkyl, substituted or unsubstituted C$_6$-C$_{20}$ aryl or substituted or unsubstituted C$_2$-C$_{20}$ heteroaryl group, and R$^c$ is selected from the group consisting of hydrogen, a substituted or unsubstituted C$_1$-C$_{20}$ alkyl, substituted or unsubstituted C$_1$-C$_{20}$ alkoxy, substituted or unsubstituted C$_2$-C$_{20}$ alkenyl, substituted or unsubstituted C$_2$-C$_{20}$ alkynyl, substituted or unsubstituted C$_1$-C$_{20}$ heteroalkyl, substituted or unsubstituted C$_6$-C$_{40}$ aryl, substituted or unsubstituted C$_7$-C$_{40}$ arylalkyl, substituted or unsubstituted C$_7$-C$_{40}$ alkylaryl, substituted or unsubstituted C$_2$-C$_{40}$ heteroaryl, and substituted or unsubstituted C$_3$-C$_{40}$ heteroarylalkyl;

substituents of R$_6$ and R$_7$, which are substituted at different positions, are alternatively interconnected to form a substituted or unsubstituted fused 4-7 atom ring; and R$_6$ and R$_7$ are not hydrogen at the same time;

X is a monoanionic monodentate ligand; and n is one of 1 and 2.

* * * * *